US007648824B2

(12) United States Patent
Nyren et al.

(10) Patent No.: US 7,648,824 B2
(45) Date of Patent: Jan. 19, 2010

(54) METHOD OF SEQUENCING DNA

(75) Inventors: Pal Nyren, Stockholm (SE); Mostafa Ronaghi, Palo Alto, CA (US); Annika Tallsjo, Uppsala (SE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 12/323,706

(22) Filed: Nov. 26, 2008

(65) Prior Publication Data

US 2009/0155801 A1 Jun. 18, 2009

Related U.S. Application Data

(62) Division of application No. 10/363,231, filed as application No. PCT/GB01/04015 on Sep. 7, 2001, now Pat. No. 7,459,311.

(30) Foreign Application Priority Data

Sep. 7, 2000 (GB) ................................ 0021977.4

(51) Int. Cl.
C12Q 1/68 (2006.01)
(52) U.S. Cl. .......................... 435/6; 435/91.1; 536/22.1; 536/24.33
(58) Field of Classification Search ....................... None
See application file for complete search history.

(56) References Cited

U.S. PATENT DOCUMENTS

| 4,654,267 | A | 3/1987 | Ugelstad et al. |
| 6,210,891 | B1 | 4/2001 | Nyren et al. |
| 6,258,568 | B1 | 7/2001 | Nyren |
| 6,828,100 | B1 | 12/2004 | Ronaghi |

FOREIGN PATENT DOCUMENTS

| JP | 2000-55917 | 2/2000 |
| WO | WO 89/09283 | 10/1989 |
| WO | WO 93/23564 | 11/1993 |
| WO | WO 94/28169 | 12/1994 |
| WO | WO 98/13523 | 4/1998 |
| WO | WO 98/28440 | 7/1998 |
| WO | WO 00/37646 | 6/2000 |
| WO | WO 00/43540 | 7/2000 |

OTHER PUBLICATIONS

Armstrong et al. (1979) Biochemistry 18:4120-4123.
Burgers, et. al. Jour. of Biol. Chem., vol. 254, No. 15, pp. 6889-6893. 1979.
Chen et al. Proc. Natl Acad. Sci. USA, vol. 94: 10756-10761. 1997.
Cook et al. Anal. Biochem., vol. 91: 557-565. 1978.
Doremus et al. Plant Physiol., vol. 87: 36-40. 1988.
Drake et al. Anal. Biochem., vol. 94: 117-120. 1979.
Eckstein, Ann. Rev. Biochem. 54: 367-402. 1985.
Ford et al. Methods in Mol. Biol., vol. 102: 3-20. 1998.
Guillory et al. Anal. Biochem. vol. 39: 170-180. 1971.
Johnson et al. Anal. Biochem. 26: 137-145. 1968.
Kajiyama et al. Biosci. Biotechnol. Biochem., vol. 58: 1170-1171. 1994.
Karamohamed et al. Protein Expression and Purification, vol. 15: 381-388. 1999.
Le Bel et al. J. Biol. Chem, vol. 255: 1227-1233. 1980.
Mizrahi et al. Biochemistry, vol. 24: 4010-4018. 1985.
Nyren et al. Anal. Biochem., vol. 151: 504-509. 1985.
Onda et al. Biosci. Biotech. Biochem., vol. 60: 1740-1742. 1996.
Outlaw. et.al., "Removal of Contaminating Nucleoside Diphosphates from Commercial Preparations of Uridine Diphosphoglucose", Analytical Biochemistry 171, 1988, pp. 104-107, Academic Press, Inc.
Reeves et al. Anal Biochem, vol. 28: 282-287. 1969.
Romaniuk et al. (1982) Journal of Biological Chemistry 257:7684-7688.
Ronaghi et al. Anal. Biochem, vol. 242: 84-89. 1996.
Ronaghi et al. Science, vol. 281: 363-365. 1998.
Ronaghi. Analytical Biochemistry, vol. 286: 282-288. 2000.
Suzuki et al. Gene, vol. 200: 149-156. 1997.
Yee et al. Biochemistry, vol. 19: 4116-4119. 1997.
Yee et al. Biochemistry, vol. 18: 4116-4120. 1979.

*Primary Examiner*—Heather G Calamita
(74) *Attorney, Agent, or Firm*—Colin L. Fairman; Fulbright & Jaworski LLP

(57) ABSTRACT

The present invention provides a method of identifying a base at a target position in a sample nucleic acid sequence, said method comprising: subjecting a primer hybridised to said sample nucleic acid immediately adjacent to the target position, to a polymerase primer extension reaction in the presence of a nucleotide, whereby the nucleotide will only become incorporated if it is complementary to the base in the target position, and determining whether or not said nucleotide is incorporated by detecting whether PPi is released, the identity of the target base being determined from the identity of any nucleotide incorporated, wherein, where said nucleotide comprises an adenine base, an α-thio triphosphate analogue of said nucleotide is used, ant the Rp isomer of said analogue and/or the degradation products of said analogue are eliminated from the polymerase reaction step.

9 Claims, 22 Drawing Sheets

SEQUENCE LISTING

<160> NUMBER OF SEQ ID NOS: 4

<210> SEQ ID NO 1
<211> LENGTH: 34
<212> TYPE: DNA
<213> ORGANISM: Artificial Sequence
<220> FEATURE:
<221> NAME/KEY: misc_feature
<222> LOCATION: ()..()
<223> OTHER INFORMATION: sequencing primer

<400> SEQUENCE: 1
ctaaaggtgc accatgactg gggttacagt catc        34

<210> SEQ ID NO 2
<211> LENGTH: 22
<212> TYPE: DNA
<213> ORGANISM: Artificial Sequence
<220> FEATURE:
<221> NAME/KEY: misc_feature
<222> LOCATION: ()..()
<223> OTHER INFORMATION: PCR primer

<400> SEQUENCE: 2
gggatcatgt aactcgcctt ga        22

<210> SEQ ID NO 3
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: PCR primer

<400> SEQUENCE: 3
cgggagggct taccatctgg        20

<210> SEQ ID NO 4
<211> LENGTH: 21
<212> TYPE: DNA
<213> ORGANISM: Artificial Sequence
<220> FEATURE:
<221> NAME/KEY: misc_feature
<222> LOCATION: ()..()
<223> OTHER INFORMATION: sequencing primer

<400> SEQUENCE: 4
tcagcaataa accagccagc c        21

METHOD OF SEQUENCING DNA

CROSS-REFERENCE TO RELATED APPLICATIONS

This application is a divisional application of U.S. patent application Ser. No. 10/363,231, filed Sep. 7, 2001, which is a national stage application under 371 of PCT/GB01/04015 filed Sep. 7, 2001, which claims priority to Great Britain Application No. 0021977.4 filed Sep. 7, 2000, the entire content of which is hereby incorporated by reference in its entirety.

FIELD OF THE INVENTION

This invention relates to improvements in methods of sequencing DNA, based on the detection of base incorporation by the release of pyrophosphate (PPi).

BACKGROUND

DNA sequencing is an essential tool in molecular genetic analysis. The ability to determine DNA nucleotide sequences has become increasingly important as efforts have proceeded to determine the sequences of the large genomes of humans and other organisms.

Techniques enabling the rapid detection of a single DNA base change, or a few base changes, are also important tools for genetic analysis, for example in clinical situations in the analysis of genetic diseases or certain cancers. Indeed, as more and more diseases are discovered to be associated with changes at the genetic level, most notably single nucleotide polymorphisms (SNPs), the need for methods of both screening for SNPs or other mutations or genetic changes (by sequencing representative genomic samples) and scoring SNPs (or other mutations/changes) grows. Thus, as well as the development of novel sequencing technologies for determining the sequence of longer stretches of DNA, the art has also seen a rapid rise in the development of technologies for detecting single (or a few) base changes. Such protocols to determine more limited sequence information, relating to only one or a few bases are termed mini-sequencing.

The method most commonly used as the basis for DNA sequencing, or for identifying a target DNA base, is the enzymatic chain-termination method of Sanger. Traditionally, such methods relied on gel electrophoresis to resolve, according to their size, DNA fragments produced from a larger DNA segment. However, in recent years various sequencing technologies have evolved which rely on a range of different detection strategies, such as mass spectrometry and array technologies.

One class of sequencing methods assuming importance in the art are those which rely upon the detection of PPi release as the detection strategy. It has been found that such methods lend themselves admirably to large scale genomic projects or clinical sequencing or screening, where relatively cost-effective units with high throughput are needed.

Methods of sequencing based on the concept of detecting inorganic pyrophosphate (PPi) which is released during a polymerase reaction have been described in the literature for example (WO 93/23564, WO 89/09283, WO98/13523 and WO 98/28440). As each nucleotide is added to a growing nucleic acid strand during a polymerase reaction, a pyrophosphate molecule is released. It has been found that pyrophosphate released under these conditions can readily be detected, for example enzymatically e.g. by the generation of light in the luciferase-luciferin reaction. Such methods enable a base to be identified in a target position and DNA to be sequenced simply and rapidly whilst avoiding the need for electrophoresis and the use of labels.

At its most basic, a PPi-based sequencing reaction involves simply carrying out a primer-directed polymerase extension reaction, and detecting whether or not that nucleotide has been incorporated by detecting whether or not PPi has been released. Conveniently, this detection of PPi-release may be achieved enzymatically, and most conveniently by means of a luciferase-based light detection reaction termed ELIDA (see further below).

It has been found that dATP added as a nucleotide for incorporation, interferes with the luciferase reaction used for PPi detection. Accordingly, a major improvement to the basic PPi-based sequencing method has been to use, in place of dATP, a dATP analogue (specifically dATPαs) which is incapable of acting as a substrate for luciferase, but which is nonetheless capable of being incorporated into a nucleotide chain by a polymerase enzyme (WO98/13523).

Further improvements to the basic PPi-based sequencing technique include the use of a nucleotide degrading enzyme such as apyrase during the polymerase step, so that unincorporated nucleotides are degraded, as described in WO 98/28440, and the use of a single-stranded nucleic acid binding protein in the reaction mixture after annealing of the primers to the template, which has been found to have a beneficial effect in reducing the number of false signals, as described in WO00/43540.

However, even with the modified and improved PPi-based sequencing methods mentioned above, there is still room for improvement, for example to increase the efficiency and/or accuracy of the procedure, or, as discussed further below, to increase the sequence read length possible. The present invention addresses these needs.

In particular, the present invention is concerned with methods of PPi-based sequencing which use an α-thio analogue of deoxy ATP (dATP) (or dideoxy ATP (ddATP)) namely an (1-thio) triphosphate (or α-thiophosphate) analogue of deoxy or dideoxy ATP, preferably deoxyadenosine [1-thio]triphosphate or deoxyadenosine α-thiotriphosphate (dATPαs) as it is also known. dATPαs (as with all α-thio nucleotide analogues) occurs as a mixture of isomers, the Rp isomer and the Sp isomer.

When dATPαS (and/or other α-thio nucleotides) are used, it has been found that the efficiency of the sequencing method decreases as the number of cycles increases, and in particular that the read length attainable is limited (e.g. to 40-50 bases). This is believed to be due to the accumulation of inhibitory substances in the reaction system. The present invention is particularly concerned with reducing or removing such inhibitory effects.

SUMMARY

More particularly, it has surprisingly been found that removing or excluding the Rp isomer of α-thio nucleotide analogues and/or the degradation products of said analogue from the polymerisation mixture improves the efficiency of PPi-based sequencing methods, and in particular, such methods based on detecting PPi by a luciferase-based ELIDA reaction.

Whilst not wishing to be bound by theory, it is believed that a number of reasons or effects may contribute to this beneficial effect of Rp isomer and/or the degradation products of the α-thio nucleotide analogue elimination on the sequencing reaction. Certain of those effects are explained further below, but in particular we believe that the Rp isomer and/or the degradation products of the α-thio nucleotide analogue are capable of inhibiting polymerase activity. Thus, it is believed that one such contributory effect may be due to the effect of the Rp isomer and/or the degradation products of the α-thio nucleotide analogue, not hitherto appreciated, in inhibiting the activity of polymerase. Hence, by excluding or removing the Rp isomer and/or the degradation products of the α-thio nucleotide analogue, this inhibitory effect may be avoided, leading to a more efficient and faster polymerisation reaction, and more even signals generated in the PPi-detection reaction. Further, by removing or excluding the Rp isomer and/or the degradation products of the α-thio nucleotide analogue, the fidelity of the DNA synthesis is increased, i.e. the number of misincorporation events is decreased.

In one aspect, the present invention thus provides a method of identifying a base at a target position in a sample nucleic acid sequence, said method comprising:

subjecting a primer hybridised to said sample nucleic acid immediately adjacent to the target position, to a polymerase primer extension reaction in the presence of a nucleotide, whereby the nucleotide will only become incorporated if it is complementary to the base in the target position, and determining whether or not said nucleotide is incorporated by detecting whether PPi is released, the identity of the target base being determined from the identity of any nucleotide incorporated, wherein, where said nucleotide comprises an adenine base, an α-thio triphosphate analogue of said nucleotide is used, and the Rp isomer of said analogue and/or the degradation products of said analogue are eliminated from the polymerase reaction step.

Use of α-trio triphosphate analogue of a nucleotide comprising an adenine base and eliminating the Rp isomer thereof and/or eliminating the degradation products of said analogue are essential features of the present invention, which this does not relate to, e.g. minisequencing reactions where only nucleotides comprising guanine, thymine or cytosine bases are added for incorporation.

Subject to the proviso that where the nucleotide comprises an adenine base (A), an α-thio triphosphate analogue of said nucleotide is used, the nucleotide may be any nucleotide capable of incorporation by a polymerase enzyme into a nucleic acid chain or molecule. Thus, for example, the nucleotide may be a deoxynucleotide (dNTP, deoxynucleoside triphosphate) or dideoxynucleotide (ddNTP, dideoxynucleoside triphosphate).

Conveniently, for sequencing purposes, guanine (G), cytosine (C), thymine (T) or adenine (A) deoxy- or dideoxy-nucleotides may be used. Thus the nucleotide may be dGTP (deoxyguanosine triphosphate), dCTP (deoxycytidine triphosphate) or dTTP (deoxythymidine triphosphate) or in place of dATP (deoxyadenosine triphosphate) its α-thiotriphosphate analogue, dATPαs (deoxyadenosine α-thiotriphosphate or deoxyadenosine [1-thio]-triphosphate as it is also known). Analogously, the nucleotides may be ddGTP, ddCTP, or dTTP, or in place of ddATP, ddATPαs.

The present invention thus requires the use of an α-thiotriphosphate analogue of an adenine nucleotide, but for the other bases (G, T or C), a native nucleotide may be used (or indeed any other nucleotide, e.g. nucleotide derivative, it is desired to use, provided that it can be incorporated by a polymerase enzyme). Thus, according to the present invention, at least an α-thio analogue of an adenine nucleotide is used.

However, it may in certain cases be desirable also to use α-thio analogues of one or more other nucleotides (i.e. of guanine, cytosine or thymine nucleotides). In any such case where an α-thio analogue of a nucleotide is used, then according to the present invention the Rp isomer of said analogue is eliminated from the polymerase reaction step. In other words, in the method of the invention, where the nucleotide is an α-thio nucleotide (e.g. deoxy- or dideoxy-nucleoside α-thiotriphosphate (dNTPαS or ddNTPαS)), the Rp isomer of said α-thio nucleotide is eliminated from the polymerase reaction step, and/or the degradation products of the NTPαS are eliminated.

For convenience, the term "deoxynucleoside α-thiotriphosphate" (dNTPαS) as used herein thus includes deoxyadenosine α-thiotriphosphate (dATPαS), deoxycytidine α-thiotriphosphate (dCTPαS), deoxyguanosine α-thiotriphosphate (dGTPα) and deoxythymidine α-thiotriphosphate (dTTPαS). Analogously, the term "dideoxy nucleotide α-thio triphosphate" includes the dideoxy equivalent. The term "dideoxynucleotide" as used herein includes all 2'-deoxynucleotides in which the 3'-hydroxyl-group is absent or modified and thus, whilst being able to be added to the primer in the presence of the polymerase, is unable to enter into a subsequent polymerisation reaction, i.e. a dideoxy nucleotide is thus a "chain terminator", and as is well known in the art, certain sequencing methods may employ such chain-terminating nucleotides.

The term "NTPαS" (nucleoside α-thiotriphosphate) is used herein to refer to all α-thiotriphosphate nucleotide analogues (i.e. α-thionucleotides) which may be used according to the present invention, and includes both ribo- and deoxyribo- (or dideoxy-) nucleotides. These include, most notably, dNTPαS and ddNTPαS.

When synthesized, α-thiotriphosphate nucleotide analogues (e.g. dd- or dNTPαS) are produced typically in two isomeric forms, the Sp and Rp isomers. An α-thiotriphosphate nucleotide analogue possesses a chiral centre, and thus the 2 species are enantiomers. The Sp isomer is the left-handed isomer, also designated the L isomer. The right-handed isomer is the Rp isomer, also known as the D-isomer (see e.g. Eckstein (1985), Ann. Rev. Biochem., 54: (367-402).

The Rp isomer of NTPαS does not act as a substrate for a polymerase enzyme, as used in the primer extension reaction. Surprisingly, however, as mentioned above, it has been found that use of the Rp isomer of NTPαS leads to inhibition of enzymes involved in the PPi-based sequencing reactions. The precise nature of these various inhibitory effects is not entirely clear, but it is believed that the Rp isomer of NTPαS itself (and possibly also the Rp isomer of NDPαS and Rp isomer of NMPαS) are responsible for the inhibitory effects observed, including, as mentioned above, inhibition of polymerase. The degradation products of NTPαS are also responsible for the inhibitory effects seen. The degradation products include, but are not limited to, NDPαS, NMPαS and any degradation products thereof. The inhibitory effects of the Rp isomer of dATPαS on nucleotide degrading enzymes and PPi detection enzymes have been investigated (see Example 2) and FIGS. 8I, 8J, 8K and 8L) and it has been shown that the Rp isomer and/or degradation products of the dATPαS do inhibit enzymes involved in nucleotide degradation and detection of PPi release.

It will be appreciated that when the target base immediately 3'- of the primer has an identical base 3'-thereto, and the polymerisation is effected with a deoxynucleotide (rather than a dideoxynucleotide) the extension reaction will add two bases at the same time and indeed any sequence of successive identical bases in the sample will lead to simultaneous incorporation of corresponding bases into the primer. However, the amount of pyrophosphate liberated will clearly be proportional to the number of incorporated bases so that there is no difficulty in detecting such repetitions.

Since the primer is extended by a single base by the procedure described above (or by a sequence of identical bases), the extended primer can serve in exactly the same way in a repeated procedure to determine the next base in the sequence, thus permitting the whole sample to be sequenced.

The method of the invention may thus be used to determine the identity (i.e. sequence) of a single base. However, conveniently, by repeating the primer extension steps in the presence of a further (successive) nucleotide, the sequence (or identity) of a further base in the sequence of the sample nucleic acid may be revealed. Accordingly, the method of the invention may be used to determine the identity of one or more bases in a sample nucleic acid (i.e. to determine the sequence of one or more bases in a sample nucleic acid).

The method of the invention thus has utility in a number of different sequencing methods and formats, including mini-sequencing procedures e.g. detection of single base changes (for example, in detecting point mutations, or polymorphisms, or allelic variations etc). Accordingly, the method of the invention may thus be used in a "full" sequencing procedure, i.e. the identification of the sequential order of the bases in a stretch of nucleotides, as well in single base detection procedures.

For example, to determine sequence information in a target nucleotide sequence (i.e. target or sample nucleic acid), different nucleotides may be added either to separate aliquots of sample-primer mixture (e.g. four aliquots, one for each of the four, A, T, G or C nucleotides) or successively to the same sample-primer mixture and subjected to the polymerase reaction to indicate which nucleotide is incorporated.

In order to sequence the sample nucleic acid, the procedure may be repeated one or more times i.e. cyclically, as is known in the art. In this way the identity of several or many bases in the sample nucleic acid may be identified, essentially in the same reaction.

Where separate aliquots are used, once it has been identified what base has been incorporated (i.e. in which aliquot incorporation has taken place), the "incorporated" base may be added to the "unreacted" aliquots, to extend the primer in all aliquots, before repeating the process (cycling) to sequence the next base. In the "successive" embodiment, a different nucleotide may be added successively until incorporation is indicated by PPi release, whereupon the procedure may be repeated.

Hence, a sequencing protocol may involve annealing a primer as described above, adding a nucleotide, performing a polymerase-catalysed primer extension reaction, detecting the presence or absence of incorporation of said nucleotide by detecting any PPi released, and repeating the nucleotide addition and primer extension steps etc. one or more times. As discussed above, single (i.e. individual) nucleotides may be added successively to the same primer-template mixture, or to separate aliquots of primer-template mixture, etc. according to choice, and the sequence information it is desired to obtain.

In order to permit the repeated or successive (iterative) addition of nucleotides in a multiple-base sequencing procedure, the previously-added nucleotide must be removed. This may be achieved by washing, or more conveniently, by using a nucleotide-degrading enzyme, for example as described in detail in WO98/28440.

Accordingly, in a principal embodiment of the present invention, a nucleotide degrading enzyme is used to degrade any unincorporated or excess nucleotide. Thus, if a nucleotide is added which is not incorporated (because it is not complementary to the target base), or any added nucleotide remains after an incorporation event (i.e. excess nucleotides) then such unincorporated nucleotides may readily be removed by using a nucleotide-degrading enzyme. This is described in detail in WO98/28440.

As will be discussed in more detail below, it has been observed that inhibitory effects due to the use of an α-thio nucleotide particularly occur (or are observed) when a nucleotide degrading enzyme is used, and that such effects may be beneficially abrogated according to the present invention, by the methods described herein.

The term "nucleotide degrading enzyme" as used herein includes any enzyme capable of specifically or non-specifically degrading nucleotides, including at least nucleoside triphosphates (NTPs), but optionally also di- and mono-phosphates, and any mixture or combination of such enzymes, provided that a nucleoside triphosphatase or other NTP-degrading activity is present. Although nucleotide-degrading enzymes having a phosphatase activity may conveniently be used according to the invention, any enzyme having any nucleotide or nucleoside degrading activity may be used, e.g. enzymes which cleave nucleotides at positions other than at the phosphate group, for example at the base or sugar residues. Thus, a nucleoside triphosphate degrading enzyme is essential for the invention. Nucleoside di- and/or mono-phosphate degrading enzymes are optional and may be used in combination with a nucleoside tri-phosphate degrading enzyme. A phosphatase used as a nucleotide degrading enzyme according to this aspect of the invention should meet several criteria, notably the inhibitory constant (Ki) for the phosphate (Pi) product of phosphatase action, should not be too low, so that the enzyme is not inhibited by accumulating phosphate. Secondly, the enzyme needs to act relatively fast and should not be too slow (certain phosphatase enzymes can act too slowly to be practical) and thirdly it should degrade all four nucleotide substrates (i.e. A, T, G and C substrates) with more or less equal efficiency. As discussed further below, ATP generated in the ELIDA reactions is preferred for PPi detection, and a nucleotide degrading enzyme useful in the invention should also efficiently degrade ATP. This leads to an efficient "turning-off" of the signal. It will be noted that not all phosphatase enzymes (e.g. alkaline phosphatases that are strongly inhibited by the product phosphate) meet these criteria, and so not all may be suitable for use as a nucleotide degrading enzyme according to the invention. However, such suitability may readily be assessed by routine experiments. The preferred nucleotide degrading enzyme is apyrase, which is both a nucleoside diphosphatase and triphosphatase, catalysing the reactions NTP→NDP+Pi and NDP→NMP+Pi (where NTP is a nucleoside triphosphate, NDP is a nucleoside diphosphate, NMP is a nucleotide monophosphate and Pi is inorganic phosphate). Apyrase may be obtained from the Sigma Chemical Company. Other possible nucleotide degrading enzymes include Pig Pancreas nucleoside triphosphate diphosphorylase (Le Bel et al., 1980, J. Biol. Chem., 255, 1227-1233). Further enzymes are described in the literature.

The nucleotide-degrading enzyme may conveniently be included during the polymerase (i.e. primer extension) reaction step. Thus, for example the polymerase reaction may conveniently be performed in the presence of a nucleotide-degrading enzyme. Although less preferred such an enzyme may also be added after nucleotide incorporation (or non-incorporation) has taken place, i.e. after the polymerase reaction step.

Thus, the nucleotide-degrading enzyme (e.g. apyrase) may be added to the polymerase reaction mixture (i.e. sample nucleic acid, primer and polymerase) in any convenient way, for example prior to or simultaneously with initiation of the reaction, or after the polymerase reaction has taken place, e.g. prior to adding nucleotides to the sample/primer/polymerase to initiate the reaction, or after the polymerase and nucleotide are added to the sample/primer mixture.

Conveniently, the nucleotide-degrading enzyme may simply be included in the reaction mixture for the polymerase reaction, which may be initiated by the addition of the nucleotide.

A further surprising feature of the present invention is the observation that use of the Rp isomer of α-thio nucleotides and/or degradation products of said α-thio nucleotides lead to inhibition of a nucleotide-degrading enzyme of the present invention, most notably apyrase. It is believed that the Rp isomer is not capable of acting as a substrate for apyrase, and accordingly that it is not degraded by the nucleotide-degrading activity of the apyrase. Alternatively, products of NTPαS degradation may be inhibitory. Thus, a situation may be created of successive accumulation of the inhibitory and inactive Rp isomer (or of inhibitory degradation products) during the sequencing procedure. Thus, a further benefit derivable from the elimination of the Rp isomer and/or degradation products of said α-thio nucleotides according to the present invention, is that inhibition of the apyrase may be reduced or avoided. This has very significant, and heretofore unpredictable, benefits on the efficiency and performance of the sequencing method, and represents a significant and surprising advantage of the present invention.

Degradation of the unincorporated nucleotides by apyrase has the benefit of producing even and well defined (e.g. narrow/defined or sharp) PPi detection signals (see further below). Where such degradation is inefficient, due to inhibition of the apyrase enzyme, this benefit is progressively lost. Thus, inhibition of apyrase is seen, directly or indirectly, as a slower nucleotide degradation rate, and consequently as a "wider" or less well-defined PPi-detection signal, in the later cycles of sequencing. In particular, in the context of ELIDA detection of PPi release, described further below, the decay in signal observed (light) is "seen" as degradation of ATP (generated in the ELIDA reactions). Thus, a slower rate of degradation of ATP is "seen". It can be inferred from this that the rate of unincorporated nucleotide degradation is also slower. Further, non-synchronised extension may result. This occurs, since the presence of undegraded unincorporated nucleotides may lead to multiple extension reactions occurring out of phase, and leading to overlapping signals (signal overlay or out of phase signals). Such non-synchronised extension thus limits the number of nucleotides which may be sequenced in a given sequencing run i.e. the read-length attainable.

The ability to sequence longer stretches of nucleic acid is a desirable goal in the sequencing field. The inhibitory effects resulting from the use of α-thio nucleotides on the enzymes present within the PPi-based sequencing methods of the present invention, leads to decreased fidelity and non-synchronised extension, thus limiting the read length attainable, i.e. the length of the nucleic acid which can be successfully sequenced. Read-length may be improved according to the present invention by eliminating the Rp isomer of the α-thio-nucleotide and/or degradation product of α-thio nucleotides.

Attainable read-length is to some extent a parameter dependent upon the acceptance criteria adopted. Cleanness of signal may be lost, but the sequence may nonetheless still be readable to a skilled and experienced practitioner. Precise read-length limits therefore are not always meaningful or cannot be applied generally, and may depend on circumstances. However, it has in certain cases been found that 50 or more, or even 100 or more (e.g. 200 or more) bases may readily be read according to the present invention. The methods of the invention are thus suitable for the sequencing of 100 bases or more. In particular, the present invention may advantageously be used in the sequencing of 50 or more, 60 or more, 70 or more or 80 or more bases.

PPi release may be detected according to the present invention in any desired or convenient way. PPi can be determined by many different methods and a number of enzymatic methods have been described in the literature (Reeves et al., (1969), Anal. Biochem., 28, 282-287; Guillory et al., (1971), Anal. Biochem., 39, 170-180; Johnson et al., (1968), Anal. Biochem., 15, 273; Cook et al., (1978), Anal. Biochem. 91, 557-565; and Drake et al., (1979), Anal. Biochem. 94, 117-120).

It is preferred to use a luciferase-based (e.g. a luciferin luciferase-based) light generating reaction to detect the release of pyrophosphate since the amount of light generated is substantially proportional to the amount of pyrophosphate released which, in turn, is directly proportional to the number of bases incorporated. The amount of light can readily be estimated by a suitable light sensitive device such as a luminometer.

Luciferase-based reactions to detect the release of PPi are well known in the art. In particular, a method for detecting PPi release based on the enzymes ATP sulphurylase and luciferase has been developed by Pyren and Lundin (Anal. Biochem., 151, 504-509, 1985) and termed ELIDA (Enzymatic Luminometric Inorganic Pyrophosphate Detection Assay). The use of the ELIDA method to detect PPi is preferred according to the present invention. The method may however be modified, for example by the use of a more thermostable luciferase (Kaliyama et al., 1994, Biosci. Biotech. Biochem., 58, 1170-1171) and/or ATP sulfurylase (Onda et al., 1996, Bioscience, Biotechnology and Biochemistry, 60: 10,1740-42). This method is based on the following reactions:

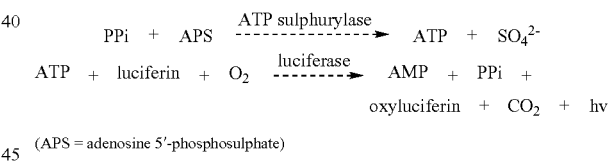

(APS = adenosine 5'-phosphosulphate)

Accordingly, it is preferred to detect PPi release enzymatically, and the preferred detection enzymes used in the PPi detection reaction are ATP sulphurylase and luciferase.

In a PPi detection reaction based on the enzymes ATP sulphurylase and luciferase, the signal (corresponding to PPi released) is seen as light. The generation of the light can be observed as a curve known as a pyrogram. Light is generated by luciferase action on the product, ATP (produced by a reaction between PPi and APS (see below) mediated by ATP sulphurylase) and, where a nucleotide-degrading enzyme such as apyrase is used, this light generation is then "turned off" by the action of the nucleotide-degrading enzyme, degrading the ATP which is the substrate for luciferase. The slope of the ascending curve may be seen as indicative of the activities of DNA polymerase (PPi release) and ATP sulphurylase (generating ATP from the PPi, thereby providing a substrate for luciferase). The height of the signal is dependent on the activity of luciferase, and the slope of the descending curve is, as explained above, indicative of the activity of the nucleotide-degrading enzyme.

Advantageously, by including the PPi detection enzyme(s) (i.e. the enzyme or enzymes necessary to achieve PPi detection according to the enzymatic detection system selected, which in the case of ELIDA, will be ATP sulphurylase and luciferase) in the polymerase reaction step, the method of the invention may readily be adapted to permit the sequencing reactions to be continuously monitored in real-time, with a signal being generated and detected, as each nucleotide is incorporated. The benefits of such an approach are discussed in more detail in WO98/13523.

Thus, the PPi detection enzymes (along with any enzyme substrates or other reagents necessary for the PPi detection reaction) may simply be included in the polymerase reaction mixture.

More particularly, to carry out this embodiment of the method of the invention, the detection enzymes are included in the polymerase reaction step i.e. in the chain extension reaction step. Thus the detection enzymes are added to the reaction mix for the polymerase step prior to, simultaneously with or during the polymerase reaction. In the case of an ELIDA detection reaction, the reaction mix for the polymerase reaction may thus include at least one nucleotide, polymerase, luciferin, APS, ATP suphurylase and luciferase. The polymerase reaction may be initiated by addition of the polymerase or, more preferably the nucleotide, and preferably the detection enzymes are already present at the time the reaction is initiated, or they may be added with the reagent that initiates the reaction. If a nucleotide degrading enzyme such as apyrase is used, it will of course be understood that polymerase addition should not follow apyrase, if nucleotides are present.

The present invention thus permits PPi release to be detected during the polymerase reaction giving a real-time signal. The sequencing reactions may be continuously monitored in real-time.

The Rp isomer and/or the degradation products of NTPαS may be eliminated according to the present invention in a number of ways, and the term "eliminated" requires simply that the Rp isomer and/or degradation products be removed or excluded from the polymerase reaction step. This may be achieved in any convenient way. For example, the Rp isomer may be excluded, by not being present in the NTPαS preparation which is added to or included in the polymerase reaction mixture. Alternatively, the NTPαS preparation may initially include the Rp isomer, but it may be removed, before, during or after, inclusion in or addition to the polymerase reaction mixture, for example by enzymic degradation. Combinations of means for eliminating the Rp isomer (e.g. removing and excluding) may also be used. Thus, the Rp isomer may be removed or excluded from the polymerase reaction step, from the step after polymerisation has occurred (i.e. the nucleotide degradation step) or the detection of nucleotide incorporation step.

The degradation products of the NTPα-S may be removed during the polymerisation step, the nucleotide degrading step or the detection of nucleotide incorporation step. For example the degradation products are eliminated by enzymic degradation.

In one embodiment of the invention, the Rp isomer may thus be eliminated by using a preparation of NTPαS which contains only the Sp isomer i.e. by using the Sp isomer of NTPαS only e.g. pure Sp isomer. Individual Rp and Sp isomers of dATPαS are available commercially (e.g. from Biolog Life Science, Bremen, Del.). Alternatively, such isomers may readily be synthesised stereo-specifically, or purified (separated) from a racemic mixture using techniques well known in the art and described in the literature (see e.g. Eckstein, supra). dATPαS, along with the α-thio analogues of dCTP, dGTP and dTTP, may be purchased from Amersham Pharmacia Biotech (Uppsala, SE).

The Rp isomer may be reduced in the reaction step to less than 10% of the total dATPαS, preferably less than 5%, more preferably less than 3% Rp isomer.

In an alternative embodiment, the Rp isomer and/or degradation products of the α-thio nucleotide analogue may be removed by using an enzyme which degrades it, notably alkaline phosphatase. In particular, preliminary experimental results lead us to believe that alkaline phosphatase is capable of degrading both isomers of NTPαS, including the Rp isomer and degradation products of NTPαS. Thus, Rp isomer and degradation products of NTPαS present in the reaction mixture, or in the NTPαS preparation, may readily be removed (degraded) by adding an alkaline phosphatase enzyme.

In a more particular embodiment, a combination of Sp isomer together with an alkaline phosphatase enzyme may be used.

Conveniently, the alkaline phosphatase may simply be included during the polymerase reaction step. This may be achieved by adding the enzyme to the polymerase reaction mixture prior to, or simultaneously with, initiation of the polymerase reaction, or after the polymerase reaction has taken place, e.g. prior to adding nucleotides to the sample/primer/polymerase mixture to initiate the reaction, or after the polymerase and nucleotide are added to the sample/primer mixture.

Alternatively, the alkaline phosphatase can be immobilized on a solid support e.g. a particulate solid support (e.g. magnetic beads) or a filter, or dipstick etc. and it may be added to the polymerase reaction mixture at a convenient time. When the Rp isomer has been degraded, the immobilised enzyme may be removed from the reaction mixture (e.g. it may be withdrawn or captured, e.g. magnetically in the case of magnetic beads), before the next nucleotide, is added. The procedure may then be repeated to sequence more bases.

Alkaline phosphatase catalyses the removal of 5'-phosphate residues from nucleoside tri-, di- and mono-phosphates (including ribo-NTPs and dNTPs and, as mentioned above the both isomers of NTPαs). Thus, not only are nucleotides (nucleoside triphosphates) degraded but also NDPs and NMPs. Shrimp, bacterial and/or calf-intestinal alkaline phosphatase are the preferred enzymes, but any suitable alkaline phosphatase enzyme may be used in the method of the invention, from any convenient source. The preferred enzyme is shrimp alkaline phosphatase. There are many commercial sources of alkaline phosphatase enzymes, or they may, if desired, be isolated from a producing organism.

The amount of alkaline phosphatase enzyme to be used will depend upon the precise reaction system used, reaction conditions etc. and can readily be determined by routine experiments. It has been found, for example, that concentrations of 50 mU to 10 U may be employed.

As mentioned above, alkaline phosphatase has an activity in degrading NDPs and NMPs as well as NTPs. It further has the benefit of acting on α-thio modified substrates also, thus including not only NTPαS, but also NDPαS and NMPαS. This activity lends a further benefit to the present invention. Thus, it has been observed that the enzyme apyrase, and also the enzyme luciferase used in the PPi detection method preferred according to the present invention, are inhibited when an NTPαS is used for nucleotide incorporation. The precise nature of the inhibitory effects observed is unclear, but may be due to NTPαS product or substrate inhibition. Thus, NTPαS may itself be inhibitory, or more likely a degradation product of NTPαS (for example resulting from apyrase action) is inhibitory. For example, it is postulated that the degradation products NDPαS and NMPαS, (in particular dADPαS and dAMPαS) produced by the action of apyrase on NTPαS added to the polymerase reaction mixture for incorporation, may be inhibitory. More particularly, it is believed that both the Sp and Rp isomers of NDPαS and/or NMPαS inhibit luciferase, and also the enzyme apyrase (see further in the Examples below). Such inhibitory substances may be removed (or reduced) by the action of alkaline phosphatase.

As mentioned above, apyrase inhibition is indicated by a slower nucleotide degradation rate, and hence an increased signal width. Non-synchronised extension may also occur, and this limits the read length attainable. Luciferase inhibition is indicated by a decrease in signal intensity. Thus, as shown further in the Examples below, inhibition of luciferase can be seen as a steady decrease in signal peak height as the nucleotides are incorporated in the later cycles of sequencing.

The effect of decreased signal intensity (luciferase inhibition) may combine with the effect of loss of signal definition (e.g. increased signal width or out of phase signals) (apyrase inhibition) to reduce the efficiency of the sequencing method, and hence its ability to provide longer read lengths. The use of alkaline phosphatase in conjunction with apyrase and dATPαS (and optionally other dNTPαS's) has the unexpected additional benefit of abrogating these significant additional sources of inhibition (namely inhibition arising from the use of NTPαS together with apyrase, e.g. due to NDPαS and/or NMPαS produced by apyrase action).

Further benefits of using alkaline phosphatase may also be available. Thus, in certain conditions or circumstances, for example long-read sequencing (e.g. over 50 cycles), other, non-thio modified, NTPs added for incorporation, may also be a source of inhibition, albeit to a lesser extent than their α-thio modified analogues. For example, preliminary results suggests that dATP may be a source of inhibition for the enzyme luciferase (see the Examples below). The action of apyrase on unincorporated NTPs results in the accumulation of degradation products, namely NDPs and NMPs (e.g. dADP, dAMP, dCTP, dCMP, dGDP, dGMP, dTDP, dTMP). In later cycles of sequencing, such products may inhibit enzymes used in the sequencing and/or PPi detection reactions e.g. apyrase and/or luciferase. Although any such inhibitory effects which may be obtained with other nucleotides will be lesser than that arising from use of NTPαS, they may still nonetheless contribute to a decreased efficiency of the system. Again, any potential problem caused by such inhibitory substances, may be removed or reduced by the action of alkaline phosphatase.

ATP is generated in the first step of the ELIDA reaction (catalysed by the enzyme ATP Sulphurylase) used as the preferred method for PPi detection. Such an ATP product (in particular, any such ATP not used in the subsequent luciferase reaction) may also act as a substrate for apyrase (or other nucleotide degrading enzyme) and hence may also lead to the generation of inhibitory products (e.g. ADP and AMP) which may inhibit luciferase, and to a lesser extent, also apyrase. Again, any such inhibitory products may be reduced or removed by the action of alkaline phosphatase.

Finally, the use of alkaline phosphatase may further have a benefit in reducing any problems caused by kinase contamination. Kinases may be contaminants of enzyme preparations used in the sequencing and PPi detection reactions described herein. The action of kinases on apyrase degradation products (i.e. NDPs or NMPs), and ATP resulting from the ATP sulphurylase reaction in the ELIDA procedure may generate NTPs which may distort the primary sequencing reaction (i.e may be incorporated by polymerase), and lead to non-synchronised extension. Alkaline phosphatase has a beneficial effect in degrading potential kinase substrates.

The sample nucleic acid (i.e. the target nucleic acid to be sequenced) may be any polynucleotide sequence it is desirable to obtain sequence information about. Thus, it may be any polynucleotide, or indeed oligonucleotide sequence. The nucleic acid may be DNA or RNA, and may be natural or synthetic. Thus, the target nucleic acid may be genomic DNA, or cDNA, or a PCR product or other amplicon etc. The target (sample) nucleic acid may be used in any convenient form, according to techniques known in the art e.g. isolated, cloned, amplified etc., and may be prepared for the sequencing reaction, as desired, according to techniques known in the art. The sample nucleic acid acts as a template for possible polymerase based extension of the primer and thus may conveniently be referred to as "template" or "nucleic acid template". The DNA may also be single or double-stranded-whilst a single-stranded DNA template has traditionally been used in sequencing reactions, or indeed in any primer-extension reaction, it is possible to use a double-stranded template; strand displacement, or a localised opening-up of the two DNA strands may take place to allow primer hybridisation and polymerase action to occur.

In the polymerase reaction, any convenient polymerase enzyme may be used according to choice, as will be described in more detail below. In the case of a, RNA template, such a polymerase enzyme may be a reverse transcriptase enzyme.

In order to repeat the method cyclically and thereby sequence the sample DNA and, also to aid separation of a single stranded sample DNA from its complementary strand, the sample DNA may optionally be immobilised or provided with means for attachment to a solid support.

Moreover, the amount of DNA present in a sample to be analysed may be small and it may therefore be desirable to amplify the DNA prior to sequencing. As mentioned above the sample DNA may thus be an amplicon.

Any desired method of in vitro or in vivo amplification may be used, e.g. PCR (or a variant or modification thereof) or Self Sustained Sequence Replication (3SR) or the ligase chain reaction (LCR) etc. Whichever method of amplification is used, it may be convenient to immobilise the amplified DNA, or provide it with means for attachment to a solid support. For example, a PCR primer may be immobilised or be provided with means for attachment to a solid support.

Immobilisation of the amplified DNA may take place as part of PCR amplification itself, as where one or more primers are attached to a support, or alternatively one or more of the PCR primers may carry a functional group permitting subsequent immobilisation, e.g. a biotin or thiol group. Immobilisation by the 5' end of a primer allows the strand of DNA emanating from that primer to be attached to a solid support and have its 3' end remote from the support and available for subsequent hybridisation with the extension primer and chain extension by polymerase.

The solid support may conveniently take the form of microtitre wells. However, any solid support may conveniently be used, including any of the vast number described in the art, e.g. for separation/immobilisation reactions or solid phase assays. Thus, the support may also comprise particles (e.g. beads), fibres or capillaries made, for example, of agarose, cellulose, alginate, Teflon or polystyrene. Magnetic particles, e.g. the superparamagnetic beads produced by Dynal AS (Oslo, Norway) also may be used as a support.

The solid support may carry functional groups such as hydroxyl, carboxyl, aldehyde or amino groups, or other moieties such as avidin or streptavidin, for the attachment of nucleic acid molecules e.g primers. These may in general be provided by treating the support to provide a surface coating of a polymer carrying one of such functional groups, e.g. polyurethane together with a polyglycol to provide hydroxyl groups, or a cellulose derivative to provide hydroxyl groups, a polymer or copolymer of acrylic acid or methacrylic acid to provide carboxyl groups or an aminoalkylated polymer to provide amino groups. U.S. Pat. No. 4,654,267 describes the introduction of many such surface coatings.

If desired, the sample may be washed after a certain number of reaction cycles e.g. 15-25, according to techniques well known in the art. Washing may be facilitated by immobilising the sample on a solid surface. Using a nucleotide-degrading enzyme, combined with Rp isomer elimination (particularly using alkaline phosphatase) however, means that washing is not absolutely necessary.

The assay technique is very simple and rapid, thus making it easy to automate by using a robot apparatus where a large number of samples may be rapidly analysed. Since the preferred detection and quantification is based on a luminometric reaction, this can be easily followed spectrophotometrically. The use of luminometers is well known in the art and described in the literature.

The method of the present invention is particularly suited for use in an array format, wherein samples are distributed over a surface, for example a microfabricated chip, and thereby an ordered set of samples may be immobilized in a 2-dimensional format. Many samples can thereby be analysed in parallel. Using the method of the invention, many immobilized templates may be analysed in this way by allowing the solution containing the enzymes and one nucleotide to flow over the surface and then detecting the signal produced for each sample. This procedure can then be repeated. Alternatively, several different oligonucleotides complementary to the template may be distributed over the surface followed by hybridization of the template. Incorporation of nucleotides may be monitored for each oligonucleotide by the signal produced using the various oligonucleotides as primer. By combining the signals from different areas of the surface, sequence-based analyses may be performed by four cycles of polymerase reactions using the various nucleotides.

The length of the extension primer is not critical and can be according to choice. It will be clear to persons skilled in the art that the size of the extension primer and the stability of hybridisation will be dependent to some degree on the ratio of A-T to C-G base pairings, since more hydrogen bonding is available in a C-G pairing. Also, the skilled person will consider the degree of sequence identity between the extension primer to other parts of the template sequence and choose the degree of stringency accordingly. Guidance for such routine experimentation can be found in the literature, for example, Molecular Cloning: a laboratory manual by Sambrook, J., Fritsch E. F. and Maniatis, T. (1989). It may be advantageous to ensure that the sequencing primer hybridizes at least one base inside from the 3' end of the template to eliminate blunt-ended DNA polymerase activity. If separate aliquots are used (i.e. 4 aliquots, one for each base), the extension primer is preferably added before the sample is divided into four aliquots although it may be added separately to each aliquot.

Alternatively, a primer with a phosphorylated 5'-end, containing a loop and annealing back on itself and the 3'-end of the single stranded template can be used. If the 3'-end of the template has the sequence region denoted T (template), the primer has the following sequence starting from the 5'-end; P-L-P'-T', where P is primer specific (5 to 30 nucleotides), L is loop (preferably 4 to 10 nucleotides), P' is complementary to P (preferably 5 and 30 nucleotides) and T' is complementary to the template sequence in the 3'-end (T) (at least 4 nucleotides). This primer can then be ligated to the single stranded template using T4 DNA ligase or a similar enzyme. This provides a covalent link between the template and the primer, thus avoiding the possibility that the hybridised primer is washed away during the protocol.

In the polymerase reaction, any convenient polymerase enzyme may be used according to choice, e.g. T7 polymerase, Klenow or Sequenase Ver. 2.0 (USB U.S.A.). Any suitable polymerase may conveniently be used and many are known in the art and reported in the literature. However, it is known that many polymerases have a proof-reading or error checking ability and that 3' ends available for chain extension are sometimes digested by one or more nucleotides. If such digestion occurs in the method according to the invention the level of background noise increases. In order to avoid this problem, a nonproof-reading polymerase, e.g. exonuclease deficient (exo$^-$) Klenow polymerase may be used and this is preferred according to the present invention. Alternatively, substances which suppress 3' digestion by polymerase, such as fluoride ions or nucleotide monophosphates, may be used. The precise reaction conditions, concentrations of reactants etc. may readily be determined for each system according to choice. However, it may be advantageous to use an excess of polymerase over primer/template to ensure that all free 3' ends are extended.

In the method of the invention, it is preferred to use a DNA polymerase with high efficiency in each extension step due to the rapid increase of background signal which may take place if templates which are not fully extended accumulate. A high fidelity in each step is also desired, which can be achieved by using polymerases with exonuclease activity. However, this has the disadvantage mentioned above that degradation of the extending strand may occur. Although the exonuclease activity of the Klenow polymerase is low, the 3' end of the primer may be degraded with longer incubations in the absence of nucleotides. An induced-fit binding mechanism in the polymerisation step selects very efficiently for binding of the correct dNTP with a net contribution towards fidelity of $10^5$-$10^6$. Exonuclease-deficient polymerases, such as (exo$^-$) Klenow or Sequenase 2.0, catalysed incorporation of a nucleotide which was only observed when the complementary dNTP was present, confirming a high fidelity of these enzymes even in the absence of proof-reading exonuclease activity. The main advantage of using (exo$^-$) Klenow DNA polymerase over Sequenase 2.0 is its lower Km for nucleotides, allowing a high rate of nucleotide incorporation even at low nucleotide concentrations. As mentioned above, it is also possible to replace all dNTPs with nucleotide analogues or non-natural nucleotides such as dNTPαS, and such analogues may be preferable for use with a DNA polymerase having exonuclease activity.

In certain circumstances, e.g. with longer sample templates, it may be advantageous to use a polymerase which has a lower $K_M$ for incorporation of the correct (matched) nucleotide, than for the incorrect (mismatched) nucleotide. This may improve the accuracy and efficiency of the method. Suitable such polymerase enzymes include the α-polymerase of *Drosophila*.

In many diagnostic applications, for example genetic testing for carriers of inherited disease, the sample will contain heterozygous material, that is half the DNA will have one nucleotide at the target position and the other half will have another nucleotide. Thus if four aliquots (i.e. four parallel reactions of the same sample) are used in an embodiment according to the invention, two will show a negative signal and two will show half the positive signal. It will be seen therefore that it is desirable to quantitatively determine the amount of signal detected in each sample. Also, it will be appreciated that if two or more of the same base are adjacent the 3'-end of the primer a larger signal will be produced. In the case of a homozygous sample it will be clear that there will be three negative and one positive signal when the sample is divided into four parallel reactions.

In carrying out the method of the invention, any possible contamination of the reagents e.g. the NTP solutions, by PPi is undesirable and may readily be avoided by including a pyrophosphatase, preferably in low amounts, in the reagent solutions. Indeed, it is desirable to avoid contamination of any sort and the use of high purity or carefully purified reagents is preferred, e.g. to avoid contamination by kinases.

Reaction efficiency may be improved by including $Mg^{2+}$ ions in the reagent (NTP and/or polymerase) solutions.

A potential problem which has previously been observed with PPi-based sequencing method arises when the DNA to be sequenced has a number of identical adjacent bases, especially three or more of the same. Further, false signals may occur due to mispriming, i.e. hybridisation of the primer not to its targeted complement within the target DNA sequence but to another region, which will result in generation of "incorporation signals" which do not reflect the identity of the target sequence. As described in WO00/43540, this may be avoided by the use of single-stranded nucleic acid binding proteins in the reaction mixture after annealing of the primer to the template.

Thus, a further preferred feature of the invention is the use of a single-stranded nucleic acid binding protein, which is included during the polymerase reaction step after primer annealing.

As mentioned above, the benefits of the present invention arise from the elimination (e.g. removal and/or exclusion) of inhibiting substances from the reaction mixture.

Thus, viewed from a different aspect, the present invention provides a method of decreasing the inhibition of polymerase in a PPi-based sequencing procedure which uses at least one NTPαS, said method comprising eliminating the Rp isomer of NTPαS and/or the degradation products of said NTPαS from the sequencing reaction mixture (i.e. the template, primer, polymerase and/or nucleotide mix).

Further, since a similar inhibiting effect has been observed for the apyrase enzyme, which may be used to degrade unincorporated nucleotides, the present invention also provides a method of decreasing the inhibition of apyrase when used in a PPi-based sequencing procedure which uses at least one NTPαS, said method comprising eliminating the Rp isomer of NTPαS and/or the degradation products of said NTPαS from the sequencing reaction.

As further mentioned above, the luciferase enzyme which is preferably used in PPi detection may be inhibited by various inhibitory substances (e.g. Rp isomer and/or degradation products) and these may advantageously be removed by the action of alkaline phosphatase. Accordingly, in a further aspect the present invention provides a method of decreasing the inhibition of luciferase when used as a detection enzyme in a PPi-based sequencing procedure, said method comprising including alkaline phosphatase in the sequencing and/or PPi detection reaction mixture. Typically, in certain embodiments of the invention NTPαS will be ATPαS (e.g. dATPαS or ddATPαS).

The invention also comprises kits for use in methods of the invention which will normally include at least the following components:

(a) a polymerase;
(b) means for detecting pyrophosphate release (preferably enzyme means, and most preferably luciferase and ATP sulphurylase, e.g. the reaction components of an ELIDA assay (see above);
(c) optionally a nucleotide-degrading enzyme (preferably apyrase);
(d) alkaline phosphatase
(e) one or more nucleotides, preferably deoxynucleotides, including, in place of an adenine nucleotide (e.g. dATP), an α-thiotriphoshate analogue of said nucleotide (e.g. dATPαS);
(f) optionally, a test specific primer which hybridises to sample nucleic acid so that the target position is in close proximity to the 3' end of the primer;

A further embodiment of the kit of the invention will normally include at least the following components:

(a) a polymerase;
(b) means for detecting pyrophosphate release (preferably enzyme means, and most preferably luciferase and ATP sulphurylase, e.g. the reaction components of an ELIDA assay (see above);
(c) optionally a nucleotide-degrading enzyme (preferably apyrase);
(d) the Sp isomer of an α-thiotriphosphate analogue of an adenine nucleotide (preferably dATPαS) and optionally one or more Sp isomers of thymine, cytosine or guanine nucleotides (preferably dGTPαS, dCTPαS or dGTPα); and
(f) optionally, a test specific primer which hybridises to sample nucleic acid DNA so that the target position is in close proximity to the 3' end of the primer;
(g) optionally, one or more modified thymine, cytosine or guanine nucleotides (preferably dTTP, dCTP, dGTP);
(h) optionally, alkaline phosphatase.

The benefits of the present invention in reducing the effects of inhibitory substances in PPi-based sequencing, improve the efficiency and reliability of the method and extend the applications in which the method can be used. Thus, techniques requiring longer reads such as genome re-sequencing, comparative EST sequencing, microbial typing and confirmatory sequencing may all be conducted by PPi-based sequencing according to the present invention.

The primer, if present in the kits, is designed so that it binds to the template nucleic acid with its 3' end in close proximity to the target nucleotide. By close proximity it is meant 1 to 30 nucleotides, preferably 1 to 20 nucleotides, more preferably 1 to 10, most preferably 1 to 5 nucleotides from the target nucleotide.

DESCRIPTION OF THE DRAWINGS

The invention will now be described by way of non-limiting examples with reference to the drawings in which.

EXAMPLE 1

Figure 1:
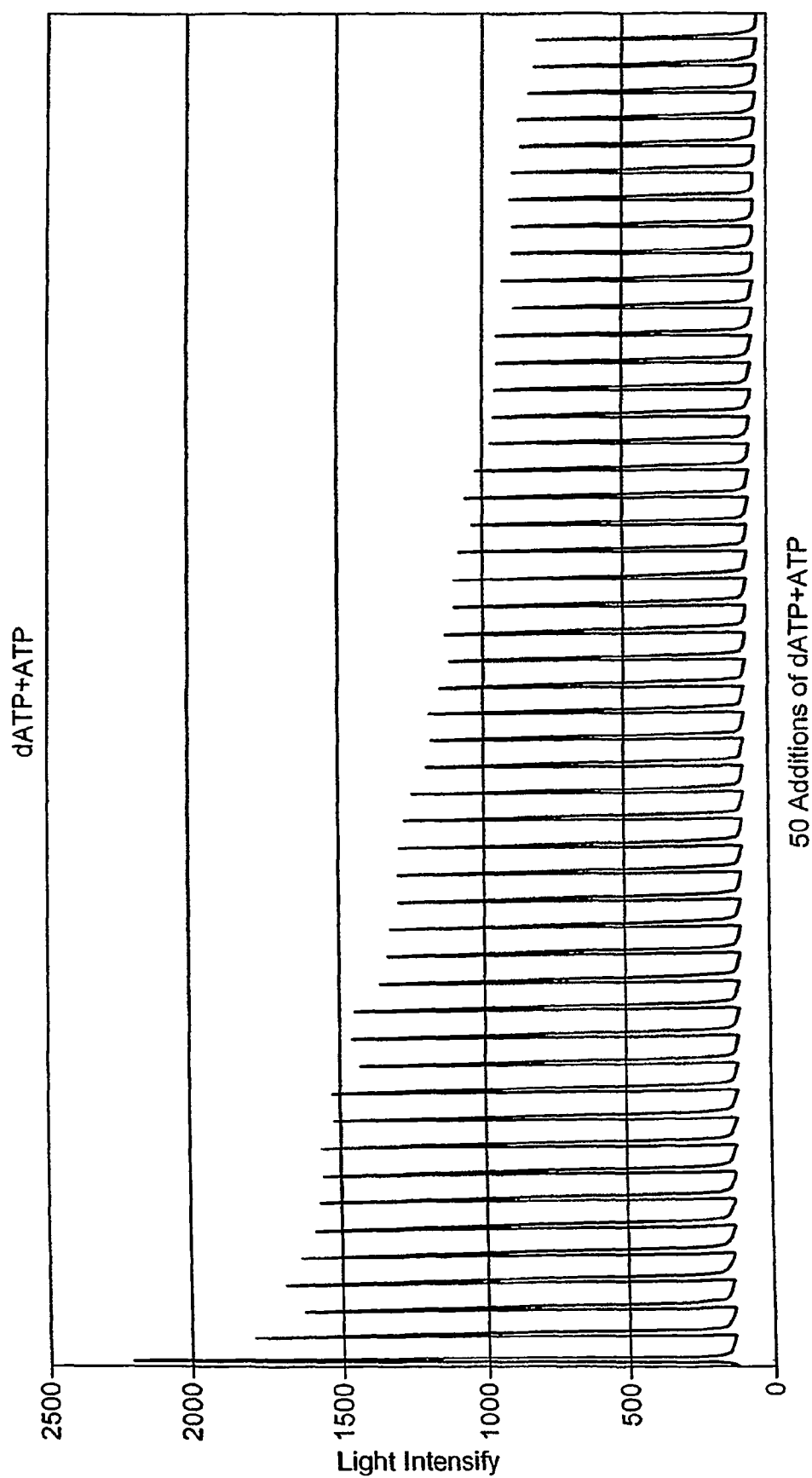
FIG. 1 shows a trace (light intensity v nucleotide addition) obtained from simulation of the effect of dATP on luciferase and apyrase, using 2 μM ATP in the nucleotide solution. In this experiment, 100 ng luciferase, 50 mU apyrase, 0.1 M Tris-acetate (pH 7.75), 0.5 mM EDTA, 5 mM magnesium acetate, 0.1% bovine serum albumin, 1 mM dithiothreitol, 0.4 mg/ml polyvinylpyrrolidone (360 000), and 100 μg/ml D-luciferin (BioThema) were used. 200 Al of 0.7 mM nucleotide (dATP) containing 2 μM ATP is dispensed into the reaction mixture as described in Example 1. The height of the ascending curve demonstrates luciferase activity and the slope of the descending curve demonstrates the apyrase activity. The PPi was detected in real time.

Investigation of the Inhibitory Effects of Different Nucleotides in PPi-based Sequencing Using an ELIDA Detection Reaction—the Effects of Alkaline Phosphatase In this Example a series of 5 experiments were carried out to examine the inhibitory effect of each of the 5 nucleotides (dATP, dATPαS, dCTP, dGTP and dTTP) on the enzymes apyrase and luciferase. A model system was used which simulated the effects of these enzymes in a PPi-based sequencing reaction. Each nucleotide was added to the luciferase/apyrase/substrate mixture, along with ATP (to provide a substrate for luciferase), and the effect of each nucleotide addition on the enzymes was monitored by observing the light signals generated from the luciferase reaction. A further two experiments demonstrate, firstly, that the inhibitory effects resulting from use of dATPαS may be abrogated in the model system by the use of alkaline phosphatase, and, secondly that alkaline phosphatase further has an additional benefit in counteracting the interfering effects of kinase enzymes on the reaction system (as demonstrated in a sequencing reaction).

The reactions were performed at room temperature in a volume of 50 μl on an automated prototype Pyrosequencer instrument (kindly supplied by Pyrosequencing AB, Uppsala, Sweden). The reaction mixture contained: 50 mU apyrase (Sigma Chemical Co., USA), 100 ng purified luciferase (BioThema, Dalaro, Sweden), 0.1 M Tris-acetate (pH 7.75), 0.5 mM EDTA, 5 mM magnesium acetate, 0.1% bovine serum albumin, 1 mM dithiothreitol, 0.4 mg/ml polyvinylpyrrolidone (360 000), and 100 μg/ml D-luciferin (BioThema). An ATP concentration of 2 μM was added to different nucleotides (dATP, dATPαS, dCTP, dGTP and dTTP), as shown in FIGS. 1 to 5 to follow the activity of luciferase and apyrase. For investigation of the effect of Shrimp Alkaline Phosphatase (Amersham Pharmacia Biotech, Uppsala, Sweden), two units of this enzyme were added to the reaction mixture—see further below. In total, 50 additions of nucleotide and ATP mixture were performed in 50 minutes. The output of light resulting from nucleotide incorporation was detected by a CCD-camera. The data was obtained in Excel format.

Seven experiments were performed. Experiments 1 to 5 investigated the effects of each of dATP, dATPαS, dCTP, dGTP and dTTP. Experiment 1 was performed using an admixture of 0.7 mM nucleotide dATP and 2 μM ATP dispensed to the reaction mixture. The trace obtained from experiment 1 is presented as FIG. 1. The height of the ascending curve demonstrates luciferase activity and the slope of the descending curve is indicative of or demonstrates apyrase activity. Note the relatively linear decrease in signal intensity, which is due to inhibition of luciferase, believed to be due to accumulation of degradation products of dATP (e.g. dAMP). It has earlier been reported that dAMP inhibits luciferase (Ford et al., 1998, Methods in Mol. Biol., 102: 3-20) and accordingly it is inferred from this that the inhibitory substance may be dAMP. Thus, luciferase inhibition is shown, when dATP is used, and this is believed to be due to the degradation products of dAMP (dATP and/or dADP).

Figure 2:
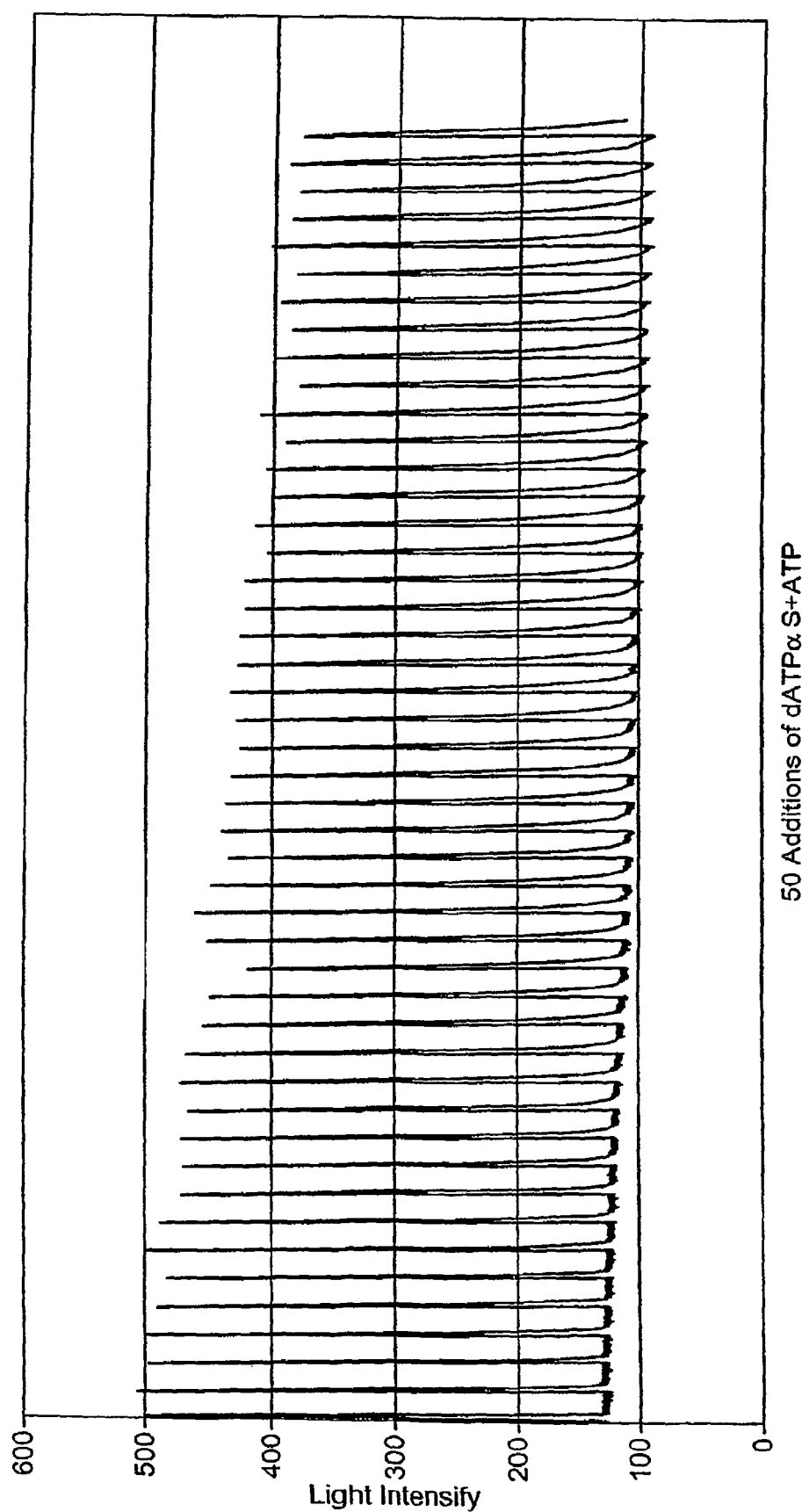
FIG. 2 shows a trace (light intensity v nucleotide addition) obtained from simulation of the effect of dATPαS on luciferase and apyrase, using 2 µM ATP in the nucleotide solution. In this experiment, 100 ng luciferase, 50 mU apyrase, 0.1 M Tris-acetate (pH 7.75), 0.5 mM EDTA, 5 mM magnesium acetate, 0.1% bovine serum albumin, 1 mM dithiothreitol, 0.4 mg/ml polyvinylpyrrolidone (360 000), and 100 µg/ml D-luciferin (BioThema) were used. 200 µl of 0.7 mM nucleotide (dATPαS) containing 2 µM ATP is dispensed to the reaction mixture as described in Example 1. The height of ascending curve demonstrates luciferase activity and the slope of descending curve demonstrates the apyrase activity.

Experiment 2 was performed using an admixture of 0.7 mM nucleotide dATPαS and 2 AM ATP dispensed to the reaction mixture. The results are shown in FIG. 2. The height of the ascending curve demonstrates luciferase activity and the slope of the descending curve demonstrates apyrase activity. Note the relatively linear decrease in signal intensity, which is due to inhibition of luciferase, believed to be caused by accumulation of inhibitory products (e.g. dAMPαS). The decrease in signal intensity after 50 cycles is 50% less than the data obtained from degradation of dATP in FIG. 1. Accordingly, it is inferred from this that just one isomer of dATPαS is inhibitory, and this is believed to be the Sp-isomer (or rather that the products of Sp isomer are inhibitory to luciferase). Apyrase is drastically inhibited in later cycles as seen by the wider peaks which are obtained. The inhibitory effect after each addition is believed to be due to accumulation of the Rp isomer of dATPαS, and also the product(s) of the degradation of the Sp isomer. It is believed that apyrase degrades only the Sp isomer and not the Rp isomer. It is speculated that the inactive isomer of dATPαS (Rp) is not recognised by luciferase since it is not degraded to form the inhibitory product.

Figure 3:
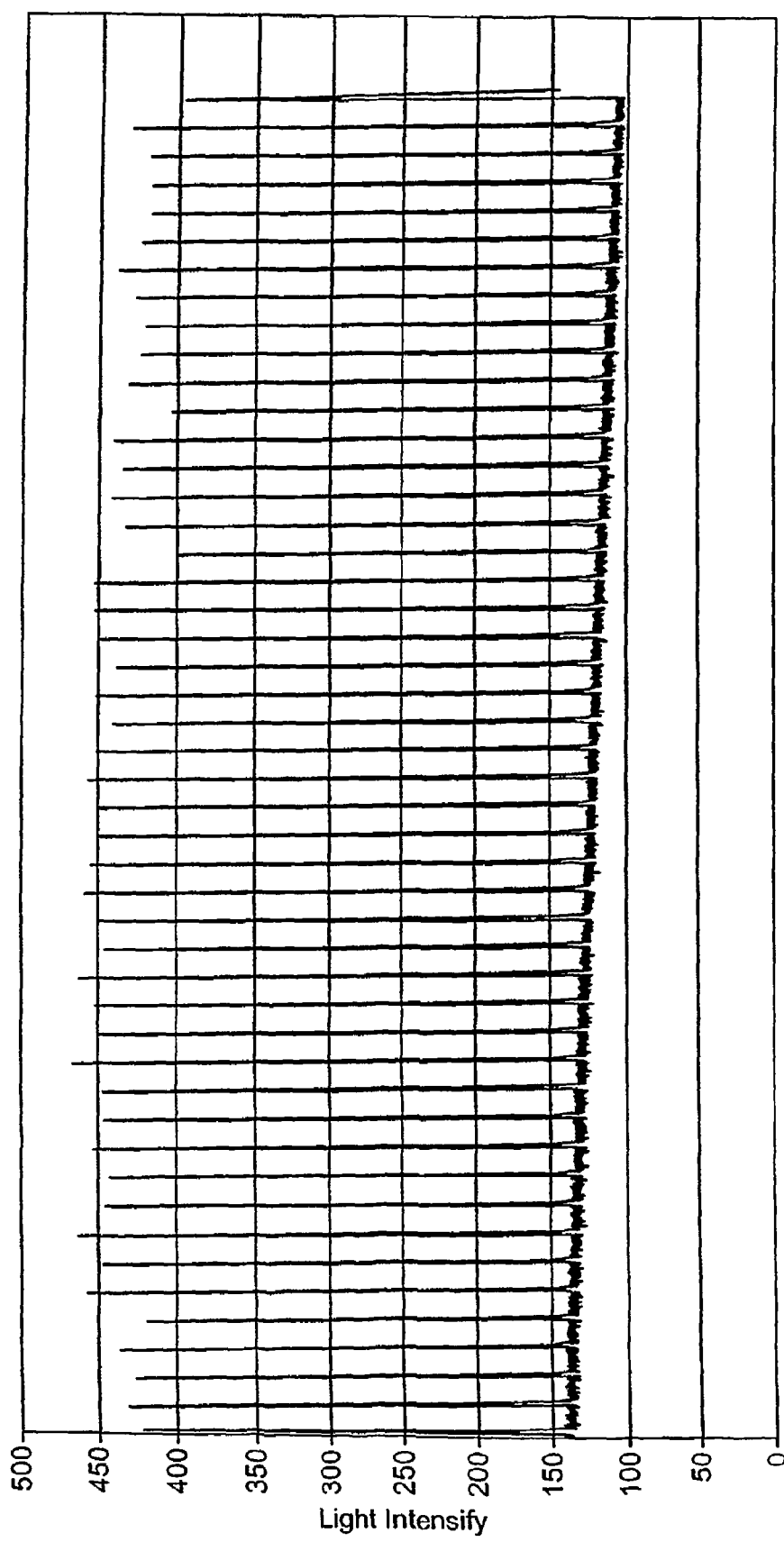
FIG. 3 shows a trace (light intensity v nucleotide addition) obtained from simulation of the effect of dCTP on luciferase and apyrase, using 2 µM ATP in the nucleotide solution. In this experiment, 100 ng luciferase, 50 mU apyrase, 0.1 M Tris-acetate (pH 7.75), 0.5 mM EDTA, 5 mM magnesium acetate, 0.1% bovine serum albumin, 1 mM dithiothreitol, 0.4 mg/ml polyvinylpyrrolidone (360 000), and 100 µg/ml D-luciferin (BioThema) were used. 200 µl of 0.2 mM nucleotide (dCTP) containing 2 µM ATP is dispensed to the reaction mixture as described in Example 1. The height of ascending curve demonstrates luciferase activity and the slope of descending curve demonstrates the apyrase activity.
Figure 4:
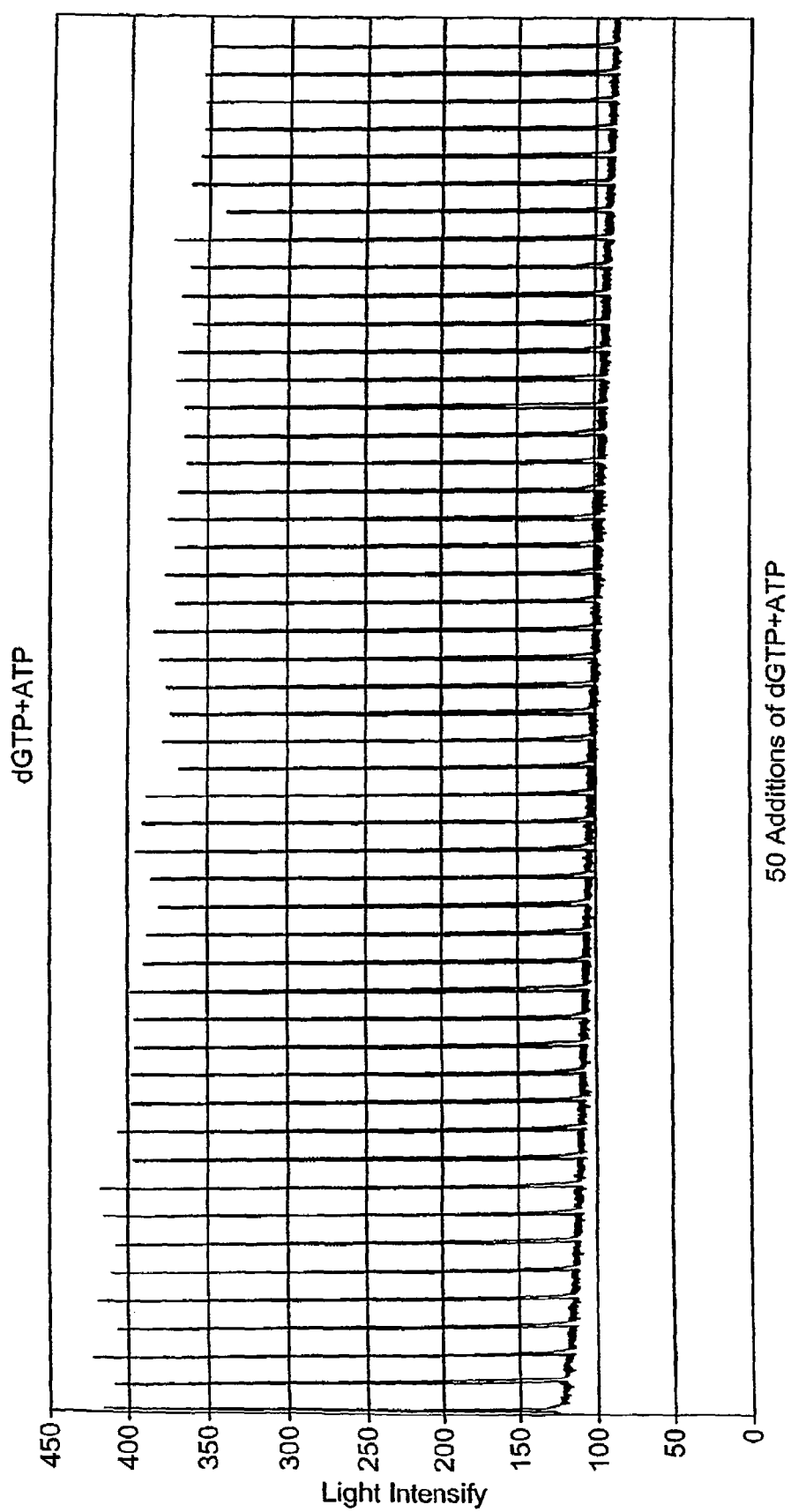
FIG. 4 shows a trace (light intensity v nucleotide addition) obtained from simulation of the effect of dGTP on luciferase and apyrase, using 2 µM ATP in the nucleotide solution. In this experiment, 100 ng luciferase, 50 mU apyrase, 0.1 M Tris-acetate (pH 7.75), 0.5 mM EDTA, 5 nM magnesium acetate, 0.1% bovine serum albumin, 1 mM dithiothreitol, 0.4 mg/ml polyvinylpyrrolidone (360 000), and 100 µg/ml D-luciferin (BioThema) were used. 200 µl of 0.16 mM nucleotide (dGTP) containing 2 µM ATP is dispensed to the reaction mixture as described in Example 1. The height of ascending curve demonstrates luciferase activity and the slope of descending curve demonstrates the apyrase activity.

Experiment 3 was performed using an admixture of 0.2 mM nucleotide dCTP and 2 AM ATP dispensed to the reaction mixture. The results are shown in FIG. 3. The height of the ascending curve demonstrates luciferase activity and the slope of the descending curve demonstrates apyrase activity. Note the relatively constant signal intensity even after 50 cycles which indicates that the products of this nucleotide do not inhibit luciferase or apyrase under the conditions used, and within the number of cycles shown.

Experiment 4 was performed using an admixture of 0.16 mM nucleotide dGTP and 2 μM ATP dispensed to the reaction. The results obtained from experiment 4 are presented in FIG. 4. The height of the ascending curve demonstrates luciferase activity and the slope of the descending curve demonstrates the apyrase activity. Note the relatively constant signal intensity even after 50 cycles which indicate that the products of this nucleotide do not inhibit luciferase or apyrase under the conditions used, and within the number of cycles shown.

Figure 5:
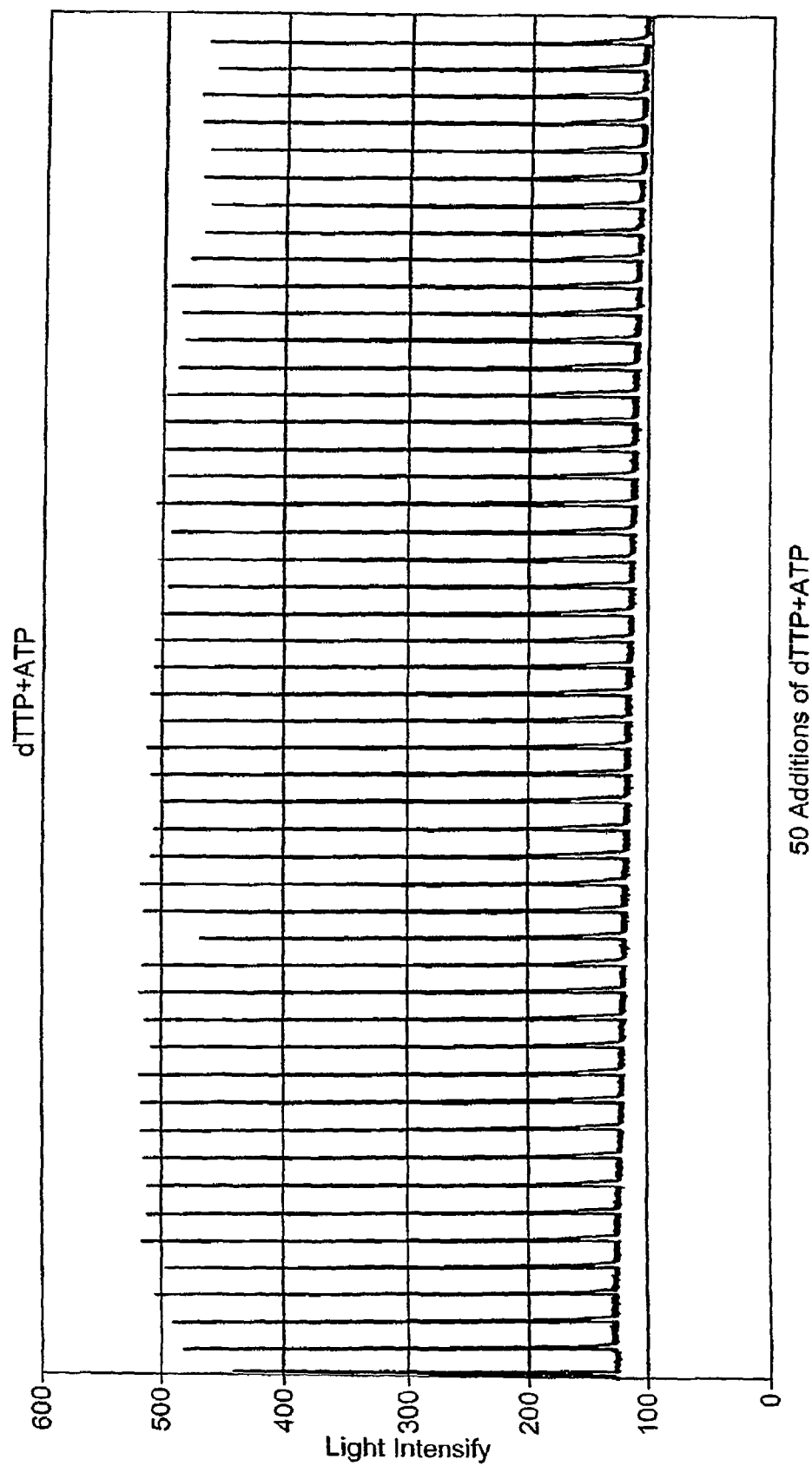
FIG. 5 shows a trace (light intensity v nucleotide addition) obtained from simulation of the effect of dTTP on luciferase and apyrase, using 2 µM ATP in the nucleotide solution. In this experiment, 100 ng luciferase, 50 mU apyrase, 0.1 M Tris-acetate (pH 7.75), 0.5 mM EDTA, 5 mM magnesium acetate, 0.1% bovine serum albumin, 1 mM dithiothreitol, 0.4 mg/ml polyvinylpyrrolidone (360 000), and 100 µg/ml D-luciferin (BioThema) were used. 200 µl of 0.8 mM nucleotide (dTTP) containing 2 µM ATP is dispensed to the reaction mixture as described in Example 1. The height of ascending curve demonstrates luciferase activity and the slope of descending curve demonstrates the apyrase activity.

Experiment 5 was performed using an admixture of 0.8 mM nucleotide dTTP and 2 μM ATP dispensed-to the reaction. The results are shown in FIG. 5. The height of ascending curve demonstrates luciferase activity and the slope of descending curve demonstrates the apyrase activity. Note the relatively constant signal intensity even after 50 cycles which indicate that the products of this nucleotide do not inhibit luciferase or apyrase, under the conditions used, and within the number of cycles shown.

Figure 6:
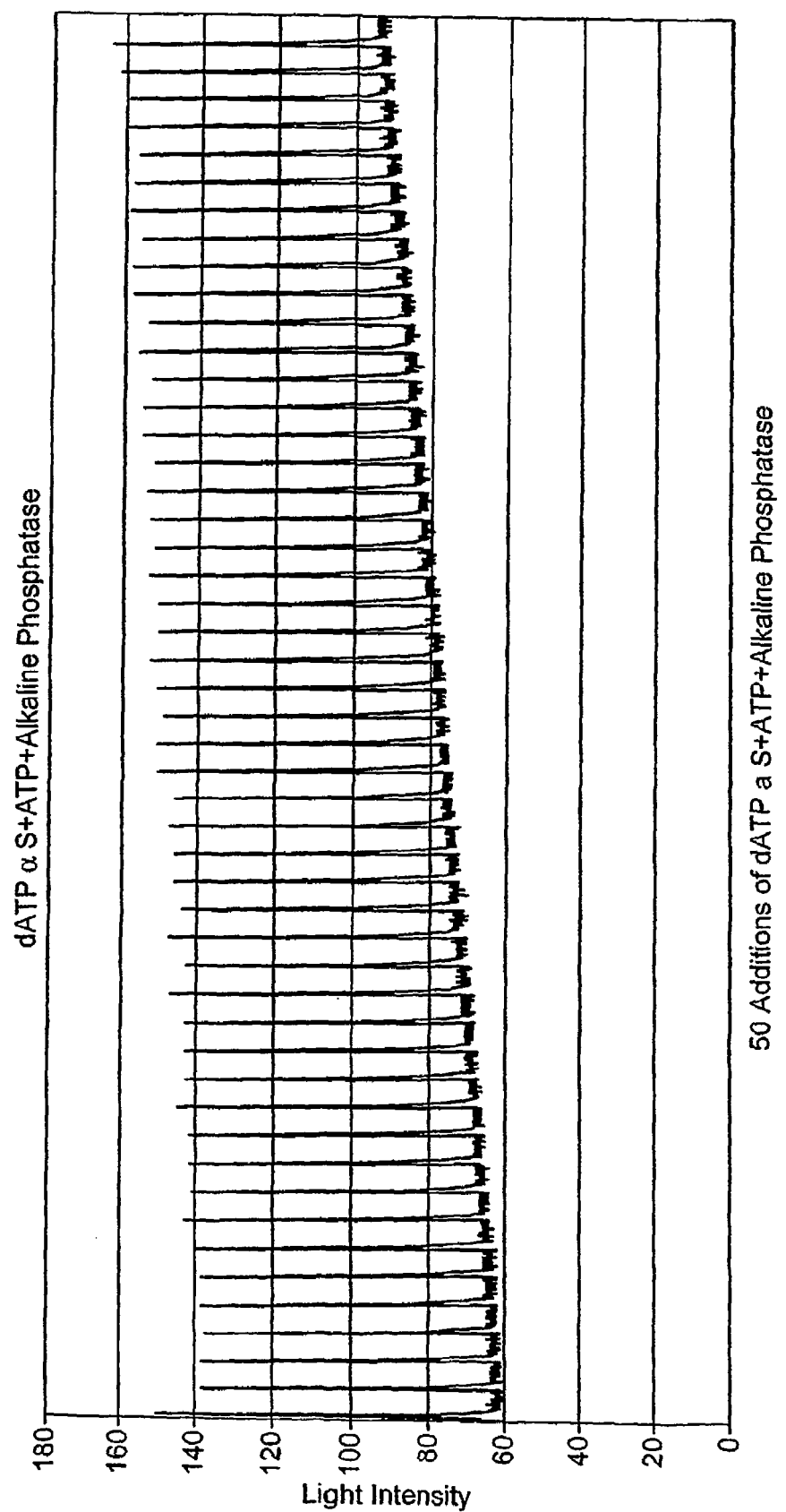
FIG. 6 shows a trace (light intensity v nucleotide addition) obtained from simulation of the effect of dATPαS on luciferase and apyrase, using 2 µM ATP in the nucleotide solution, in the presence of alkaline phosphatase. In this experiment, 100 ng luciferase, 50 mU apyrase, 0.1 M Tris-acetate (pH 7.75), 0.5 mM EDTA, 5 mM magnesium acetate, 0.1% bovine serum albumin, 1 mM dithiothreitol, 0.4 mg/ml polyvinylpyrrolidone (360 000), 100 µg/ml D-luciferin (BioThema), and 1 U alkaline phosphatase were used. 200 gl of 0.7 mM nucleotide (dATPαS) containing 2 µM ATP is dispensed to the reaction mixture as described in Example 1. The height of ascending curve demonstrates luciferase activity and the slope of descending curve demonstrates the apyrase activity.

Experiment 6 investigated the reduction in inhibition effected by the addition of alkaline phosphatase to the reaction mixture. This experiment was performed similarly as for Experiment 2, using an admixture of 0.7 mM nucleotide dATPαS and 2 μM ATP dispensed to the reaction mixture. The results are shown in FIG. 6. The height of the generated peak demonstrates luciferase activity and the slope of the descending curve demonstrates the apyrase activity. Note the efficiency of nucleotide degradation as compared with FIG. 2. It can be seen that the signal width remains constant even after 50 cycles indicating lack of apyrase inhibition, and hence the high efficiency of alkaline phosphatase in preventing this inhibition (believed to be due to its action in degrading both isomers (i.e. the Rp and Sp isomers) of dATPα). No decrease in signal intensity is observed, indicating no inhibition of luciferase. This is believed to be due to the effect of alkaline phosphatase in degrading the products of dATPαS (thus removing the inhibitory elements). The experimental conditions for FIGS. 2 and 6 are the same except for addition of 2 U AP in the reaction mixture in Experiment 6. Thus, the results of Experiment 6 show that alkaline phosphatase can remove inhibitory substances from the reaction system, thus improving the performance of the luciferase and apyrase enzymes.

Figure 7A:
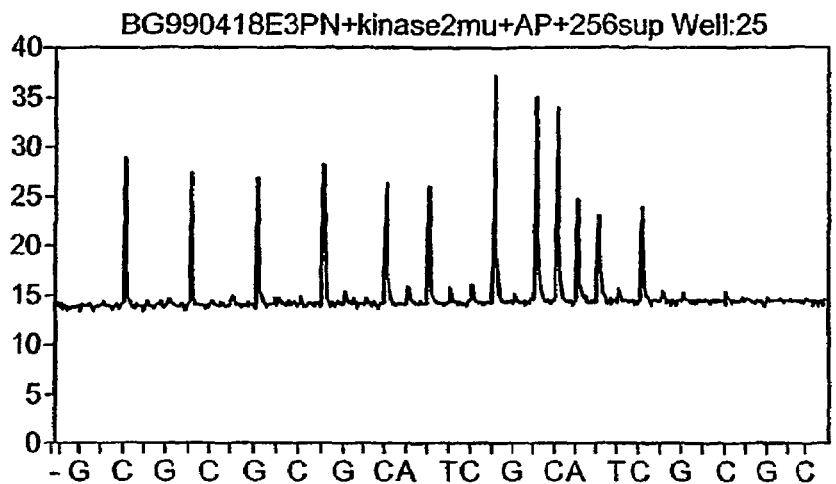
FIG. 7 shows three traces (light intensity v nucleotide addition) obtained in DNA sequencing reactions using 1 pmol of primed oligonucleotide template; the reaction system contained 10 U Klenow DNA polymerase, 25 mU ATP sulphurylase and 0.1 M Tris-acetate (pH 7.75), 0.5 mM EDTA, 5 mM magnesium acetate, 0.1% bovine serum albumin, 1 mM dithiothreitol, 0.4 mg/ml polyvinylpyrrolidone (360 000), and 100 µg/ml D-luciferin (BioThema); and A) 100 ng luciferase and 50 mU apyrase; B) 100 ng luciferase, 50 mU apyrase and 2 mU nucleoside diphosphate kinase; C) 100 ng luciferase, 50 mU apyrase, 2 mU nucleoside diphosphate kinase and 2 U alkaline phosphatase. The arrows on B indicates the false signals appearing as a result of kinase activity in the system, which are removed by addition of alkaline phosphatase in the experiment shown in C.
Figure 7B:
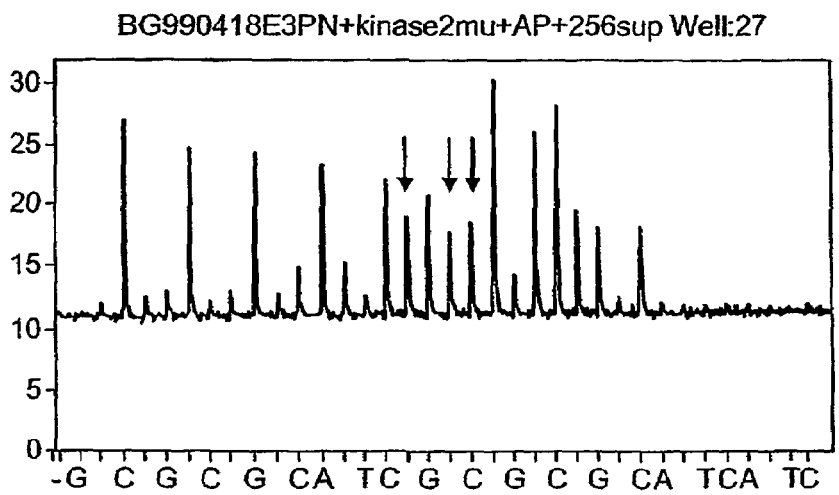
Figure 7C:
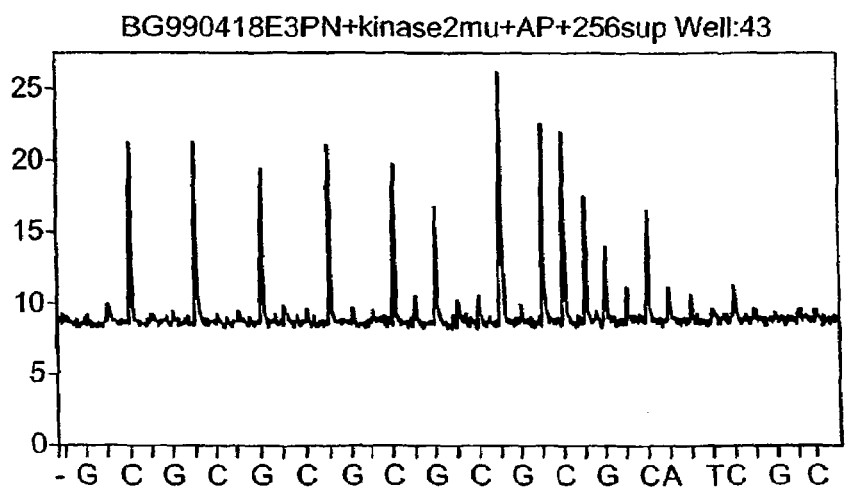

Experiment 7 investigated the inhibitory effects of nucleotides and kinases upon a sequencing reaction, and the reduction of these effects using alkaline phosphatase. For investigation of the effect of kinase, 2 mU of kinase (Sigma Chemicals) was added to the sequencing reaction mixture containing: 0.5 μmol primed synthetic template E3PN/NUSPT (Ronaghi et al. Science, 1998), 10 U exonuclease-deficient Klenow DNA polymerase (Amersham Pharmacia Biotech, Uppsala, Sweden), 40 mU apyrase (Sigma Chemical Co., USA), 100 ng purified luciferase (BioThema, Dalaro, Sweden), 15 mU of recombinant produced ATP sulfurylase, 0.1 M Tris-acetate (pH 7.75), 0.5 mM EDTA, 5 mM magnesium acetate, 0.1% bovine serum albumin, 1 mM dithiothreitol, 5 μM adenosine 5-phosphosulfate (APS), 0.4 mg/ml polyvinylpyrrolidone (360 000), and 100 μg/ml D-luciferin (BioThema). The sequencing procedure was carried out by stepwise elongation of the primer-strand upon sequential addition of Sp-dATPαS (Biolog Life Science, Bremen, Del.), dCTP, dGTP, and dTTP (Amersham Pharmacia Biotech) and simultaneous degradation of nucleotides by apyrase. To study the effect of alkaline phosphatase on kinase activity, 2 mU of kinase enzyme and 2 U of alkaline phosphatase were added to the above admixture. The output of light resulting from nucleotide incorporation was detected by a CCD-camera. The data was obtained in Excel format. FIG. 7a shows the results of the sequencing reaction in the absence of added kinase or alkaline phosphatase. FIG. 7b shows a trace of the results of the sequencing reaction in the presence of 2 mU of nucleoside diphosphate kinase. The arrow indicates the false signals that are generated.

Thus, it can be seen that the addition of alkaline phosphatase to the polymerisation reaction mixture removes the false signals generated by kinase contamination, by removing the substrates for the kinase from solution.

EXAMPLE 2

Inhibitory Effects of dATPαS on PPi-based Sequencing

In this example, the inhibitory effect of dATPαS on a PPi-based sequencing reaction with ELIDA detection (known as Pyrosequencing) was investigated by preincubating the reaction mixture in the absence of template with varying amounts of the normal (i.e. racemic) dATPαS (containing both Rp and Sp isomers), or the pure Sp isomer of dATPαS. After preincubation, template was added and a normal "Pyrosequencing™", reaction was carried out.

Materials and Methods

The "normal" dATPαS was taken from the PSQ 96 SNP Reagent kit supplied by Pyrosequencing AB (Uppsala, SE). The pure Rp and Sp isomers were purchased from Biolog Life Science (Bremen, Germany). The reaction mixture also included Enzyme mix (DNA polymerase, ATP-sulphurylase, apyrase and luciferase) and Substrate mix (luciferin and APS), from the PSQ 96 SNP Reagent kit supplied by Pyrosequencing AB. The template was an oligonucleotide (interactiva, Ulm, Germany) from which the following sequence could be read after annealing of a sequencing primer: CTAAAGGTGCACCATGACTGGGGTTACAGTCATC.

The pure isomer samples were diluted to the same concentration as the dATPαS in the PSQ 96 SNP Reagent kit. For preincubation, 0, 5, 10 or 20 µl of each A-sample (normal dATPαS or the Rp or Sp isomer) was added to a mixture containing 5 µl Enzyme mix, 5 µl Substrate mix in a total volume of 45 µl. The reaction was carried out in the 96 well plate delivered with the PSQ 96 SNP Reagent kit. The reaction was incubated at room temperature, in the dark for 10 minutes. After this, 1.5 µmol in 5 µl annealed oligonucleotide template was added to each well and the plate was transferred from the PSQ 96 instrument, where a normal "Pyrosequencing™" reaction was carried out (omitting addition of Enzyme and Substrate mixes).

Figure 8:
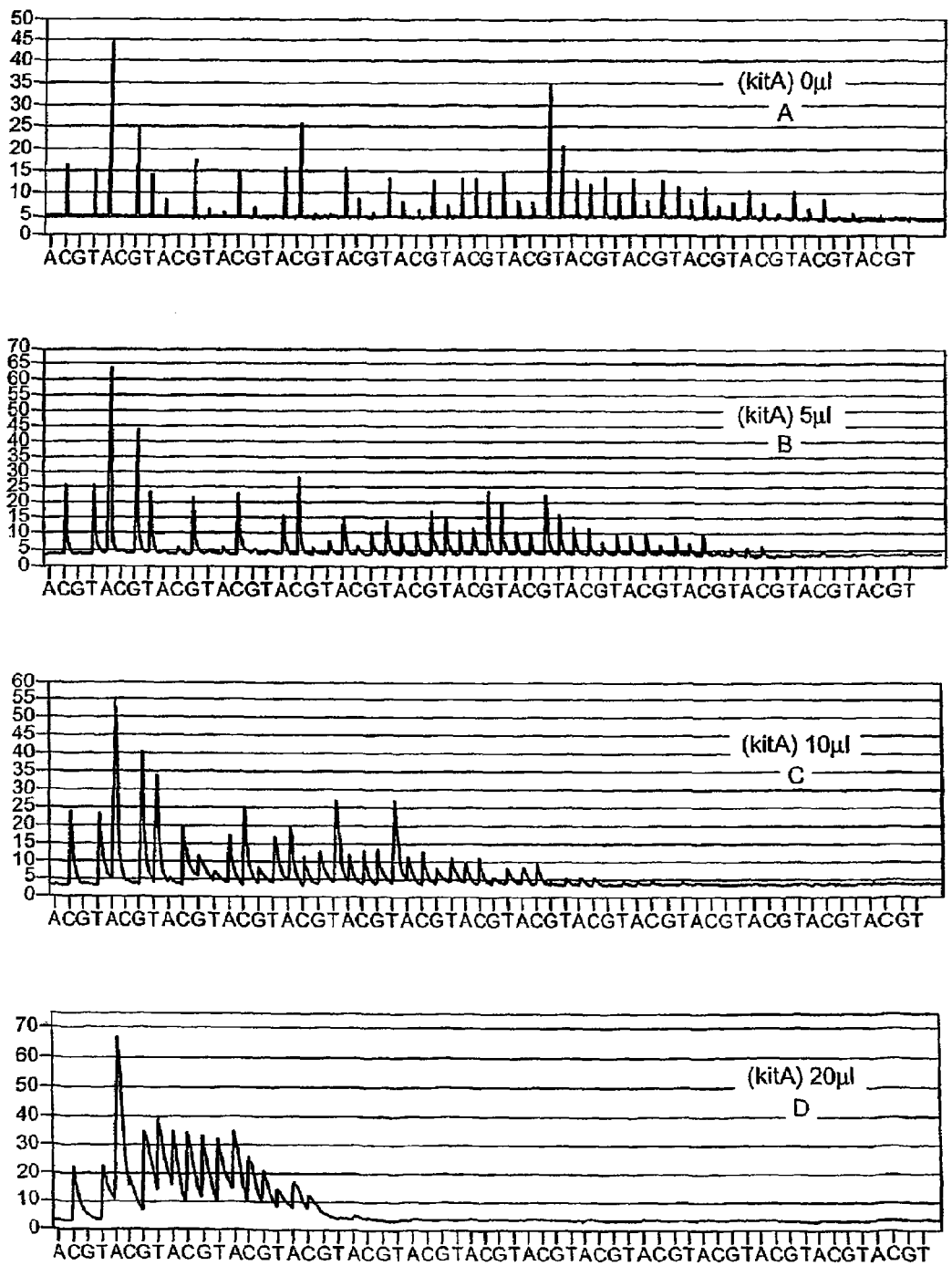
FIG. 8 presents traces (light intensity v nucleotide addition) showing the effects of pre-incubating a PPi-sequencing reaction mixture (in the absence of template) with varying amounts of "normal" (i.e. racemic) dATPαS (containing both Rp and Sp isomers) ((A) 0 µl; (B) 5 µl; (C) 10 µl; (D) 20 µl) or the pure Sp isomer of dATPαS ((E) 0 µl; (F) 5 µl; (G) 10 µl; (H) 20 µl) or the pure Rp isomer of DATPαS ((I) 0 µl; (J) 5 µl; (K) 10 µl; (L) 20 µl). After pre-incubation, template was added and the PPi-based sequencing reaction was performed as described in Example 2.
Figure 8:
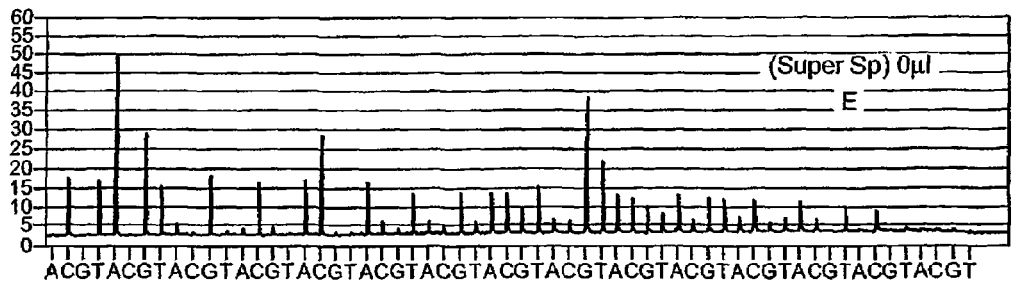
Figure 8:
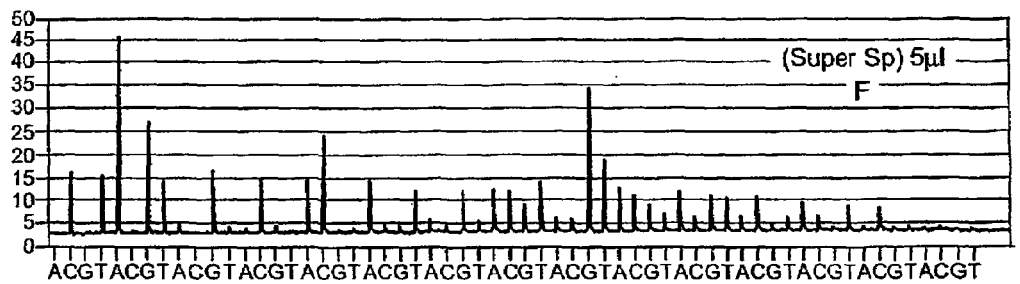
Figure 8:
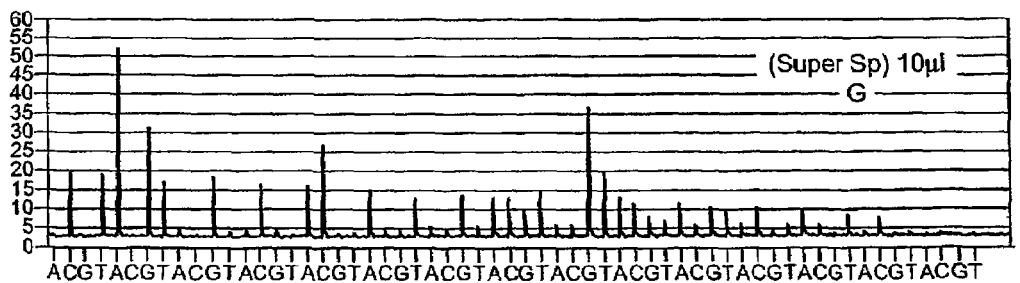
Figure 8:
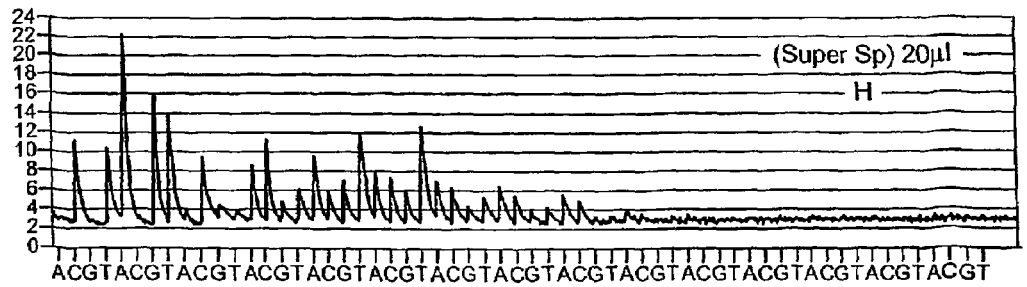
Figure 8:
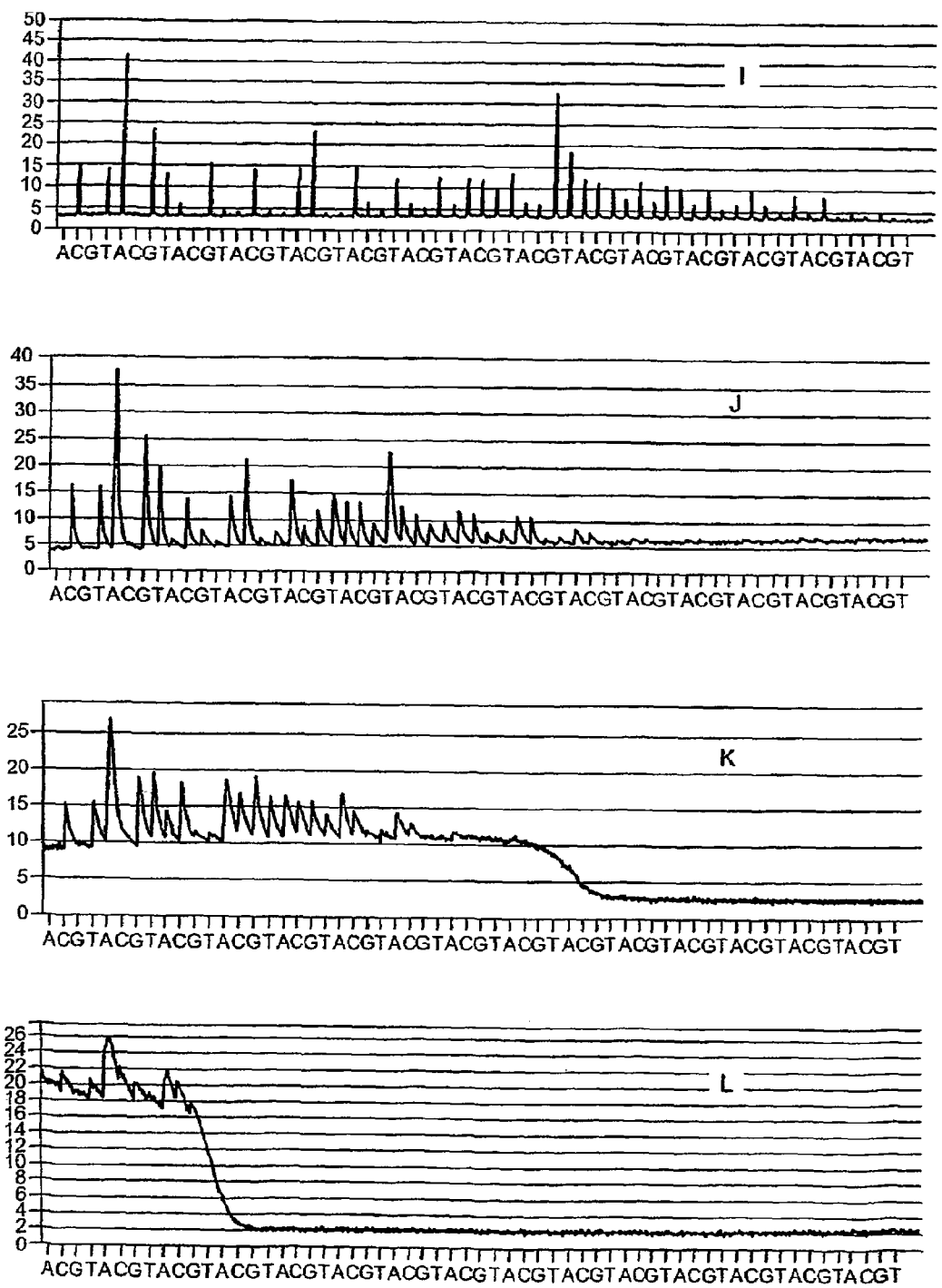

The results are shown in FIG. 8. Using normal (i.e. racemic) dATPαS, it can be seen that pre-incubation with 5 µl (FIG. 8B) 10 µl (FIG. 8C) or 20 µl (FIG. 8D) results in progressively severe inhibition of the sequencing reaction (as compared with 0 µl of dATPαS added (FIG. 8A)). Some loss of signal intensity (peak height) and more significantly, loss of signal definition (e.g. broader, less defined and less clean signals) can be seen. Thus, it can be seen that apyrase inhibition is particularly occurring. Even more pronounced inhibition is seen when the Rp isomer is used (see FIG. 8J). This effect was significantly reduced when using the pure Sp isomer in place of racemic dATPαS or Rp isomer of dATPαS, as seen from FIG. 8F (5 µl), FIG. 8G (10 µl) and FIG. 8H (20 µl) (compared to 0 Al (FIG. 8E)). The pure Rp isomer has a severe effect on all enzymes involved in the ELIDA detection (FIGS. 8I and 8J). Apyrase inhibition is indicated by increased signal width. This can clearly be seen in FIGS. 8J to 8L, most clearly it is demonstrated on FIG. 8K. Luciferase inhibition is indicated by decreased signal intensity. As can be seen on FIG. 8K, the signal intensity is decreased in comparison with FIG. 8I, indicating that luciferase is being inhibited.

A similar experiment was also performed where the preincubation was carried out comparing "normal" dATPαS with dCTP, dGTP or dTTP, all from a prototype to the PSQ 96 SNP Reagent kit. As control, only 1×TE (dilution buffer for the dNTPs) was added. The template was the same as above, but 2 pmol were added to each well.

The results obtained (not shown) clearly showed no negative effect from preincubation with dCTP, dGTP or dTTP, but confirmed a severe negative effect from dATPαS, mainly on apyrase.

EXAMPLE 3

PPi-based DNA Sequencing with and without Rp-dATPαS

In this Example, two sequencing experiments were performed using the same template (a PCR product of the standard cloning plasmid pUC19), with and without the Rp isomer of dATPαS (i.e. using firstly a racemic mixture of dATPαS, and secondly pure Sp-dATPαS).

Single Stranded Template Preparation

The standard plasmid pUC19 was used to generate the template by PCR. In brief, PCR primers GGGATCATG-TAACTCGCCTTGA (Upper primer, biotinylated position 1345) and CGGGAGGGCTTACCATCTGG (lower primer, position 1648), (where positions 1648–1345=303 bp) were used in a PCR reaction on pUC19 to generate a fragment of 303 bp in length. Fifty microliters of biotinylated PCR product was immobilized onto 20 µL streptavidin-coated super paramagnetic beads (Dynabeads M-280-streptavidin, Dynal AS, Oslo, Norway) by incubation at 43° C. for 30 minutes. Single-stranded DNA was obtained by incubating the immobilized PCR product in 5 µl 0.1 M NaOH for 4 minutes. The immobilized strand was resolved in 8 µl H$_2$O plus 1 µl annealing buffer (100 mM Tris-Ac$_2$ (pH 7.75), 20 mM MgAc$_2$). Single-stranded DNA corresponding to 50 µl PCR product was hybridized to 10 pmol sequencing primer (TCAG-CAATAAACCAGCCAGCC) at 70° C. for 3 minutes followed by incubation at room temperature for 5 minutes. (After annealing of the sequencing primer, the length of single-stranded template remaining is 211 bp.) The primed PCR product was added to the Pyrosequencing reaction mixture containing: 0.1 M Tris-Ac$_2$ (pH 7.75), 0.05% Tween 20, 10 U exonuclease deficient (exo$^-$) Klenow DNA polymerase, 40 mU apyrase (Sigma Chemical Co. St. Louis, Mo., USA), 0.8 µg purified luciferase (BioThema, Dalaro, Sweden), 15 mU recombinant ATP sulfurylase (Karamohamed et al., 1999), 0.5 µg single-stranded DNA binding protein (Amersham Pharmacia Biotech., Uppsala, Sweden), 0.5 mM EDTA, 5 mM MgAc$_2$, 0.1% bovine serum albumin (BioThema), 1 mM dithiothreitol, 5 µM adenosine 5'-phosphosulfate (Sigma Chem. Co.), 0.4 mg/ml polyvinylpyrrolidone (360 000), and 100 µg/ml D-luciferin (BioThema) in a total volume of 50 µl.

Pyrosequencing™

Pyrosequencing™ was performed at room temperature on an automated Pyrosequencer prototype model (Pyrosequencing AB, Uppsala, Sweden; www.pyrosequencing.com) at a dispensing pressure of 600 mbar with 8 msec open time and 60 sec cycle time. The sequencing procedure was carried out by stepwise elongation of the primer-strand upon cyclic dispensation of the different deoxynucleoside triphosphates (Amersham Pharmacia Biotech). In one experiment (shown in FIG. 9), a racemic mixture of dATPαS ("normal" dATPαS) is used, (along with dCTP, dGTP and dTTP) and in the second experiment pure Sp isomer of dATPαS is used. The output of light resulting from nucleotide incorporation was detected by a photomultiplier. The data was obtained in Microsoft Excel and is shown in FIGS. 9 and 10.

Figure 9:
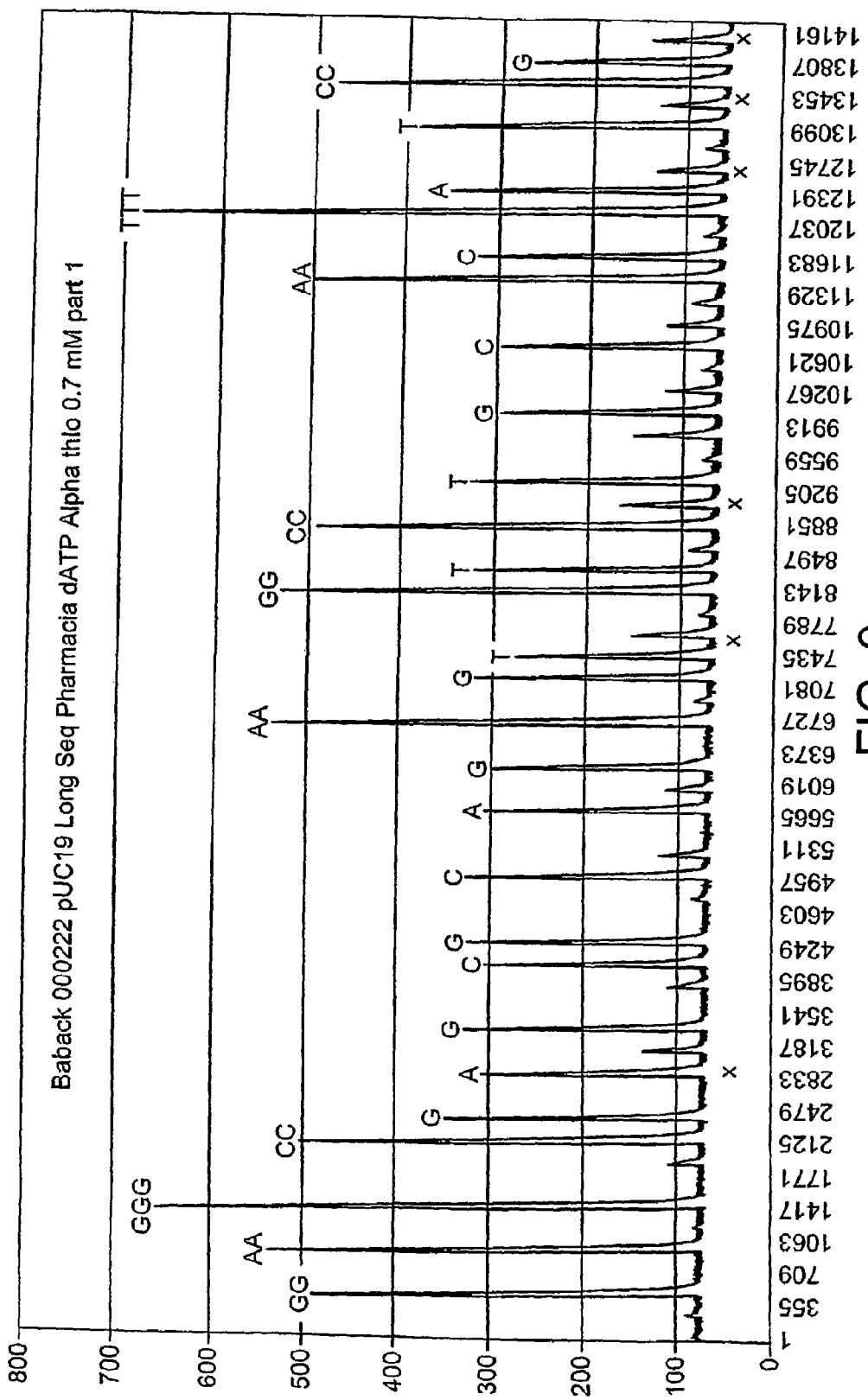
FIG. 9 is a trace (light intensity v nucleotide addition) showing the results of a DNA sequencing reaction on a pUC19-derived template wherein the four different nucleotides are added stepwise to the template hybridized to a primer. A mixture of the Rp and Sp isomers of dATPαS is used. The template/primer was incubated with 10 U (exo⁻) Klenow and 40 mU apyrase, and other components of the sequencing/PPi detection reaction as described in Example 3. The reaction was started by the addition of the first nucleotide, and the nucleotides were added in a stepwise fashion. The PPi released was detected in real time by luciferase.
Figure 9:
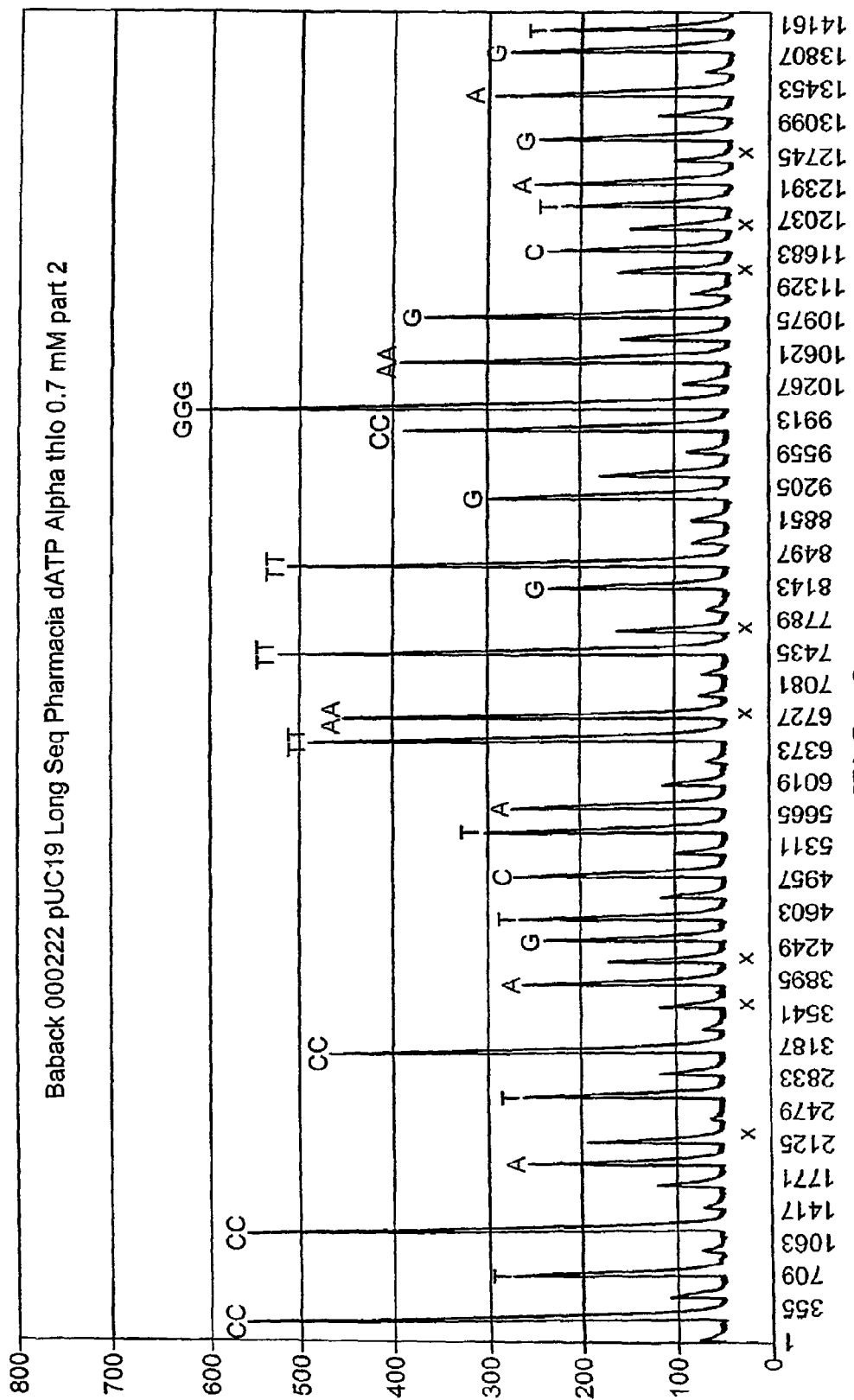
Figure 9:
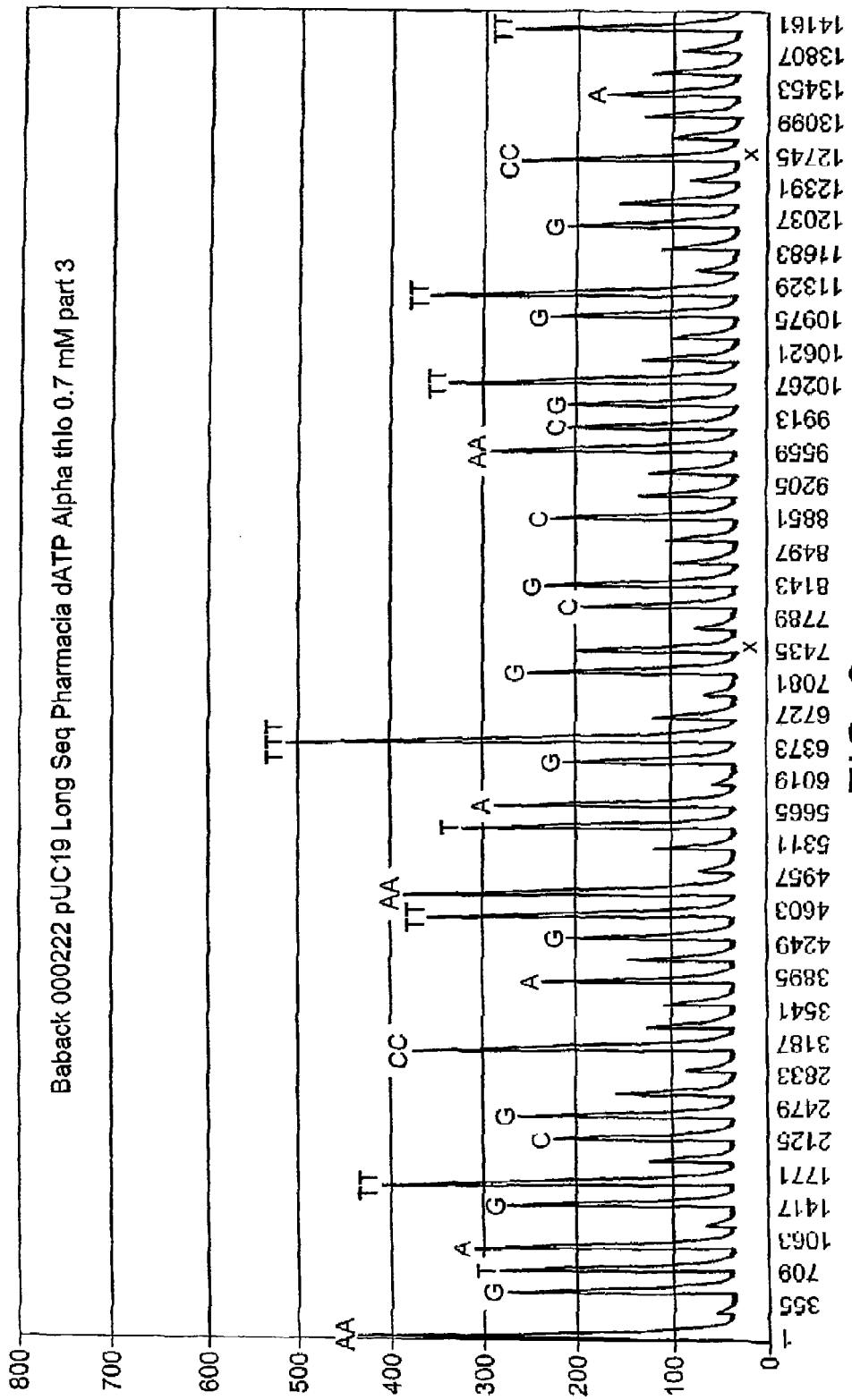
Figure 9:
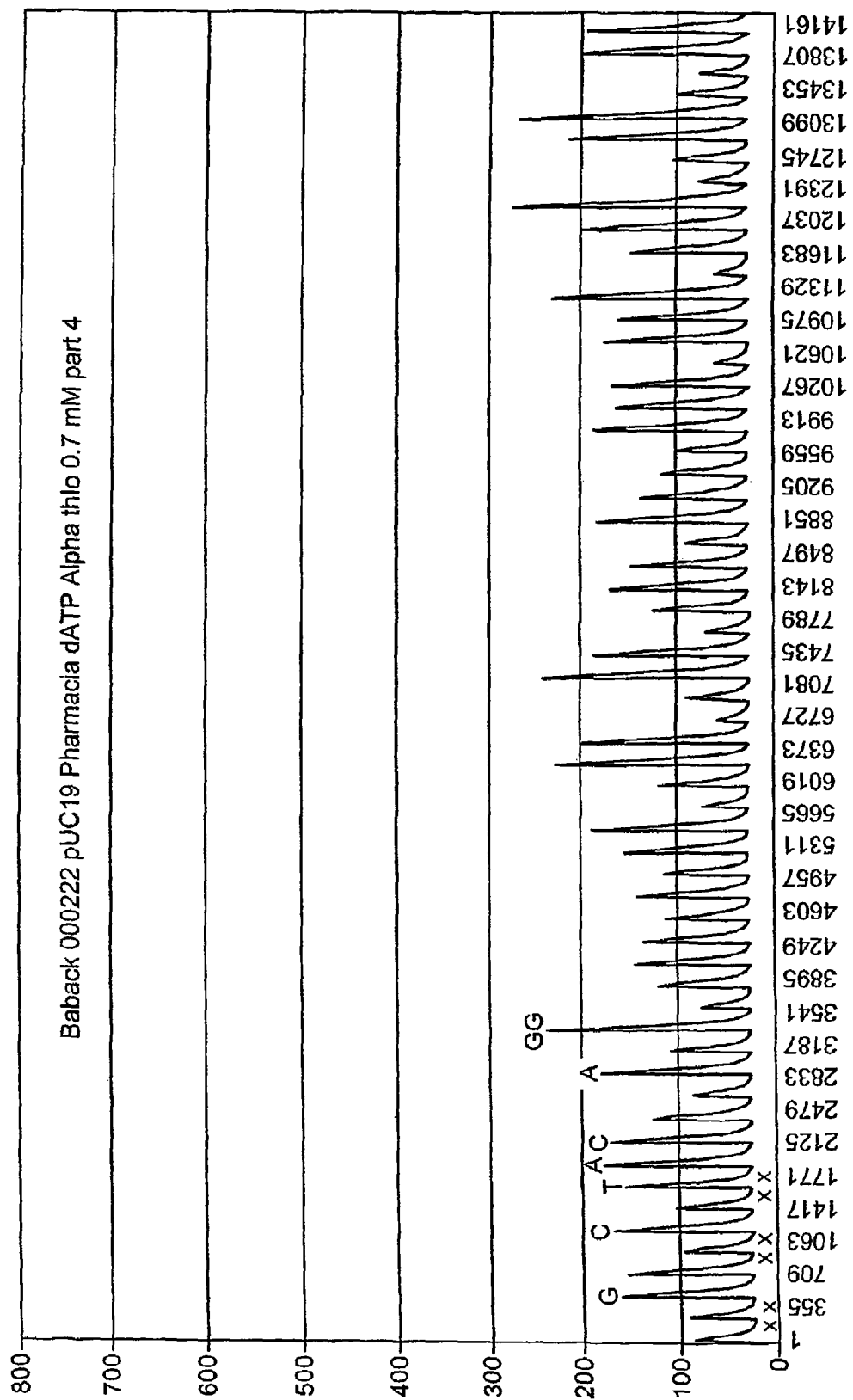
Figure 9:
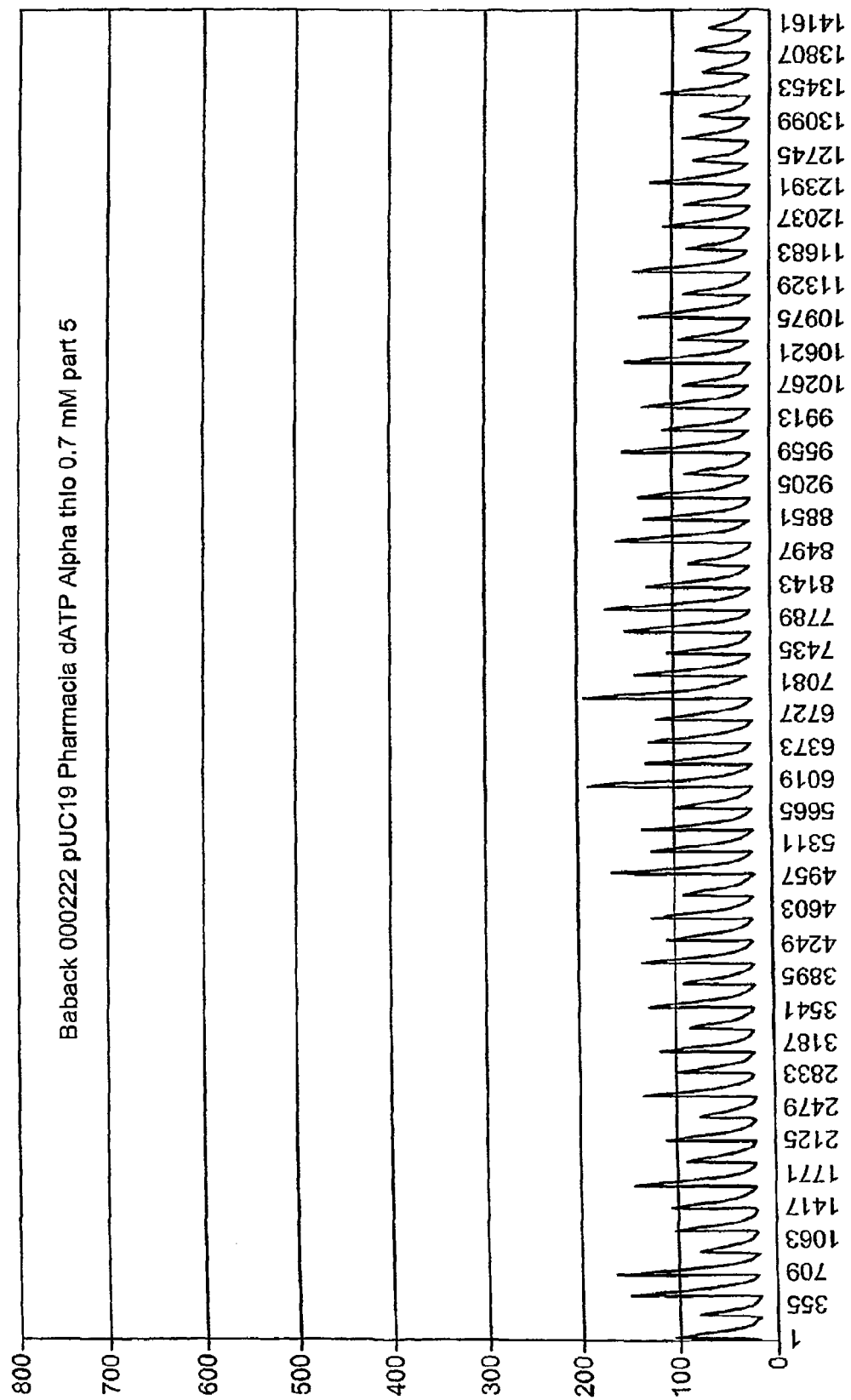
Figure 9:
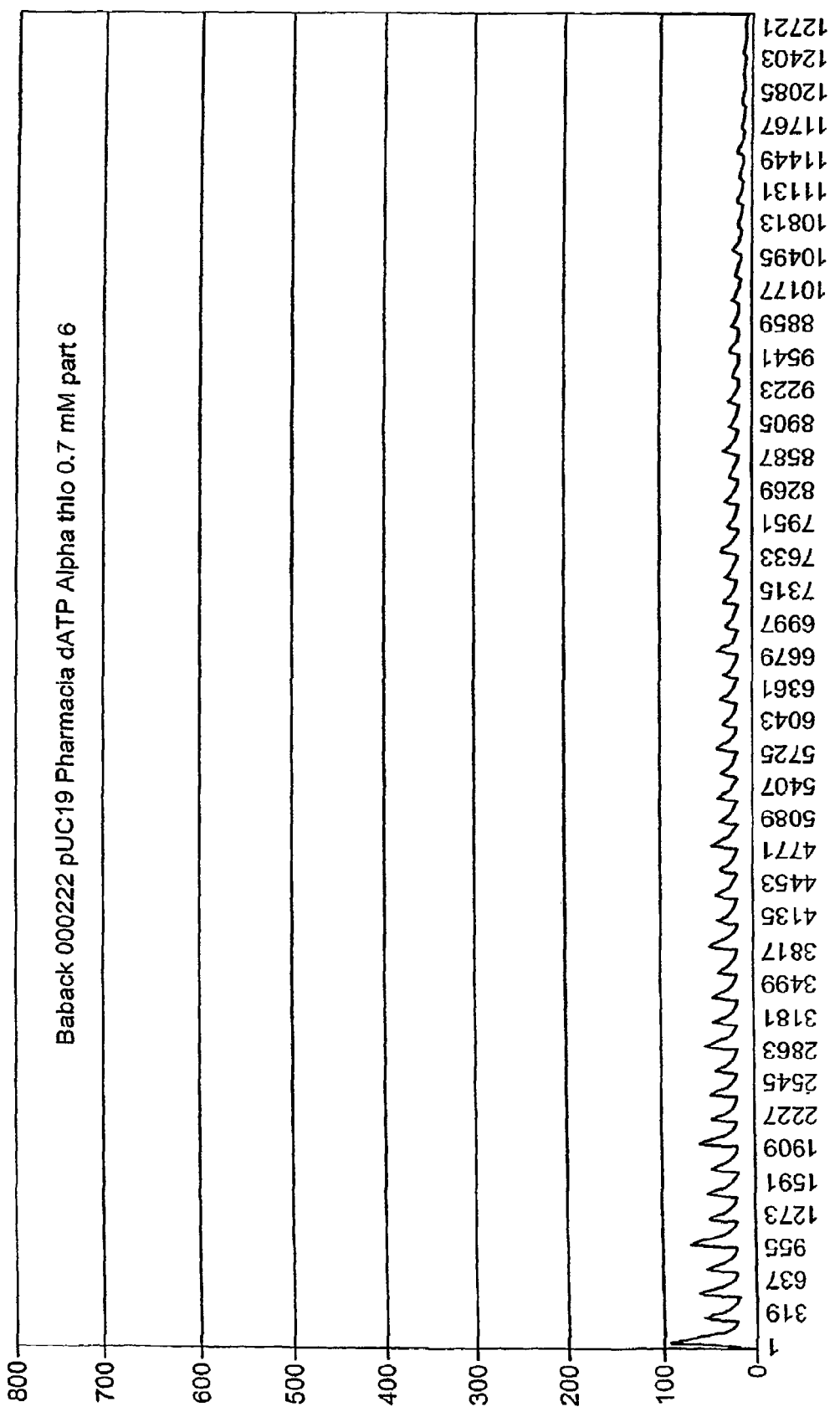
Figure 10:
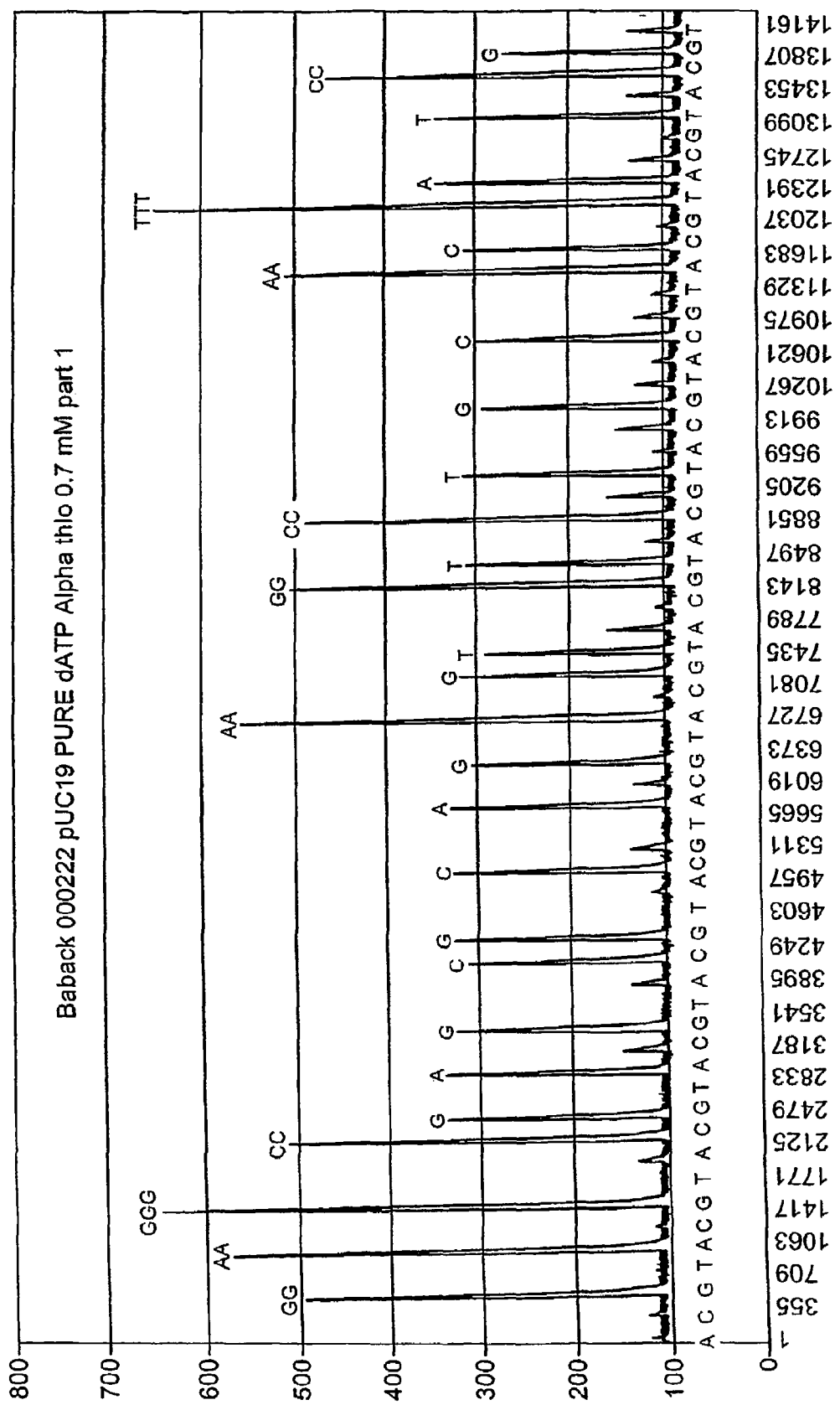
FIG. 10 is a trace (light intensity v nucleotide addition) showing the results of a DNA sequencing reaction on a pUC19-derived template wherein the four nucleotides are added stepwise to the template hybridized to the primer. Only the pure Sp isomer of d-ATPαS was used. The template/primer was incubated with 10 U (exo⁻) Klenow and 40 MU apyrase and other components of the sequencing/PPi detection reaction as described in Example 3. The reaction was started by the addition of the first nucleotide, and nucleotides were then added in a stepwise fashion. The PPi released was detected in real time by luciferase.
Figure 10:
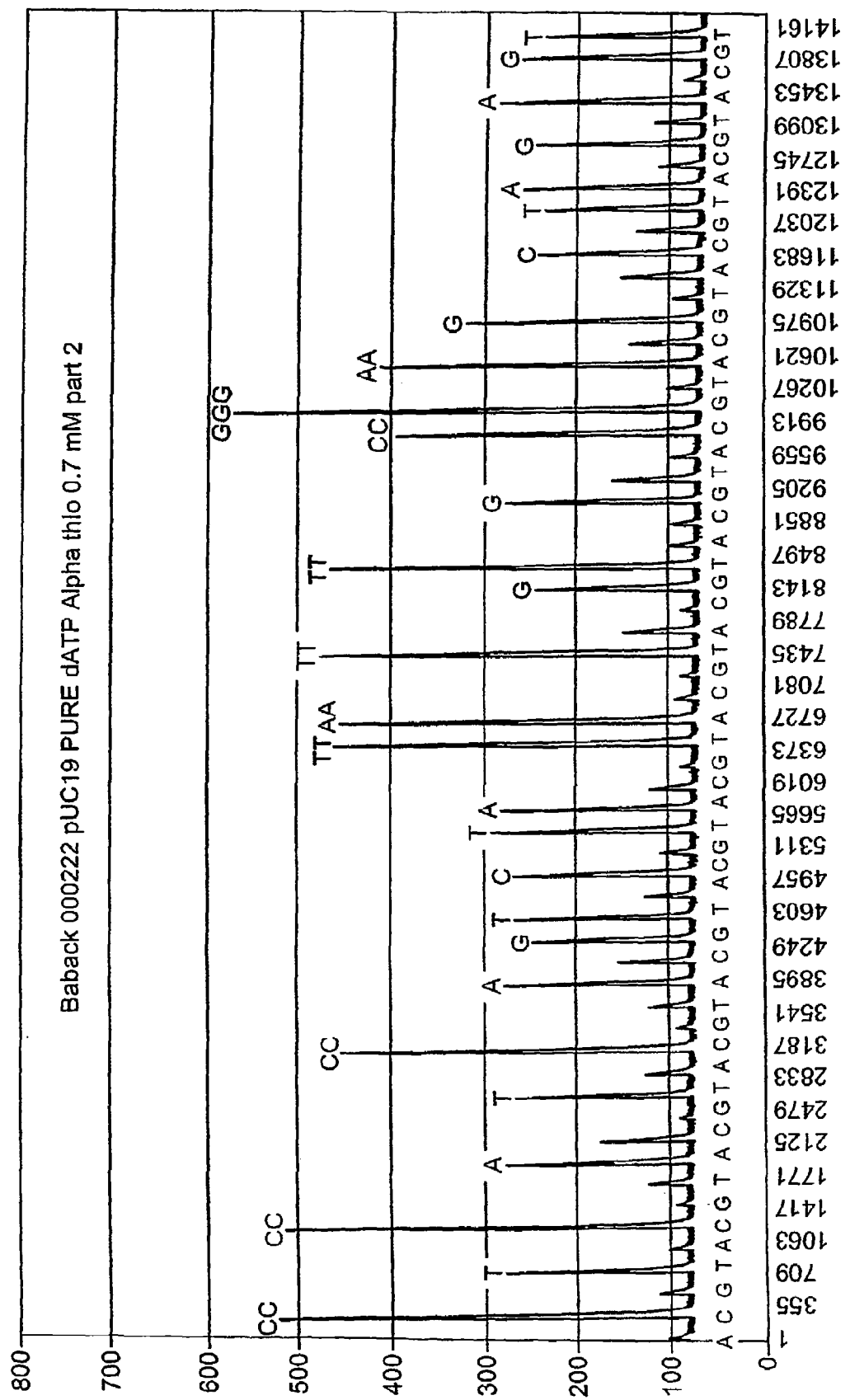
Figure 10:
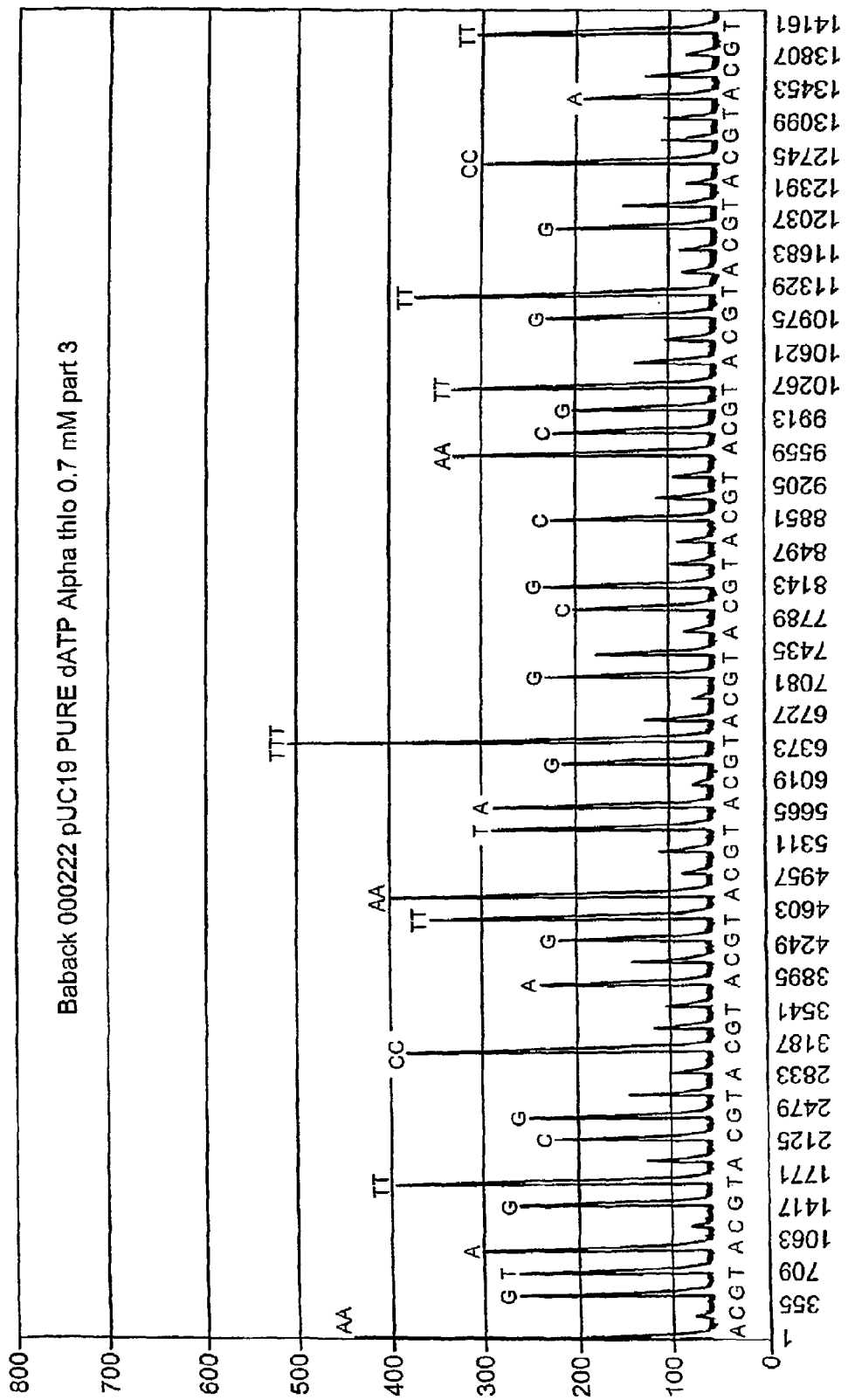
Figure 10:
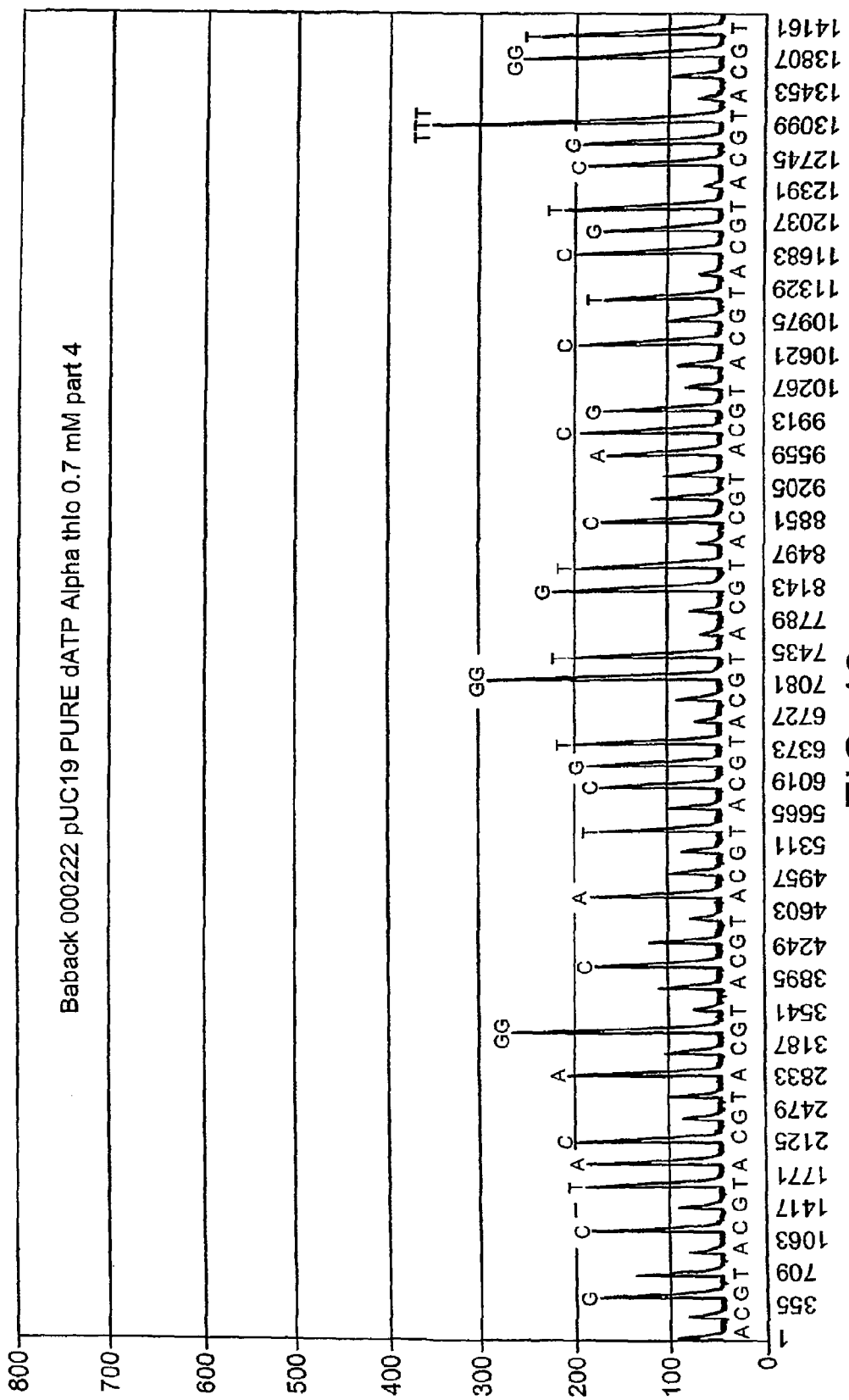
Figure 10:
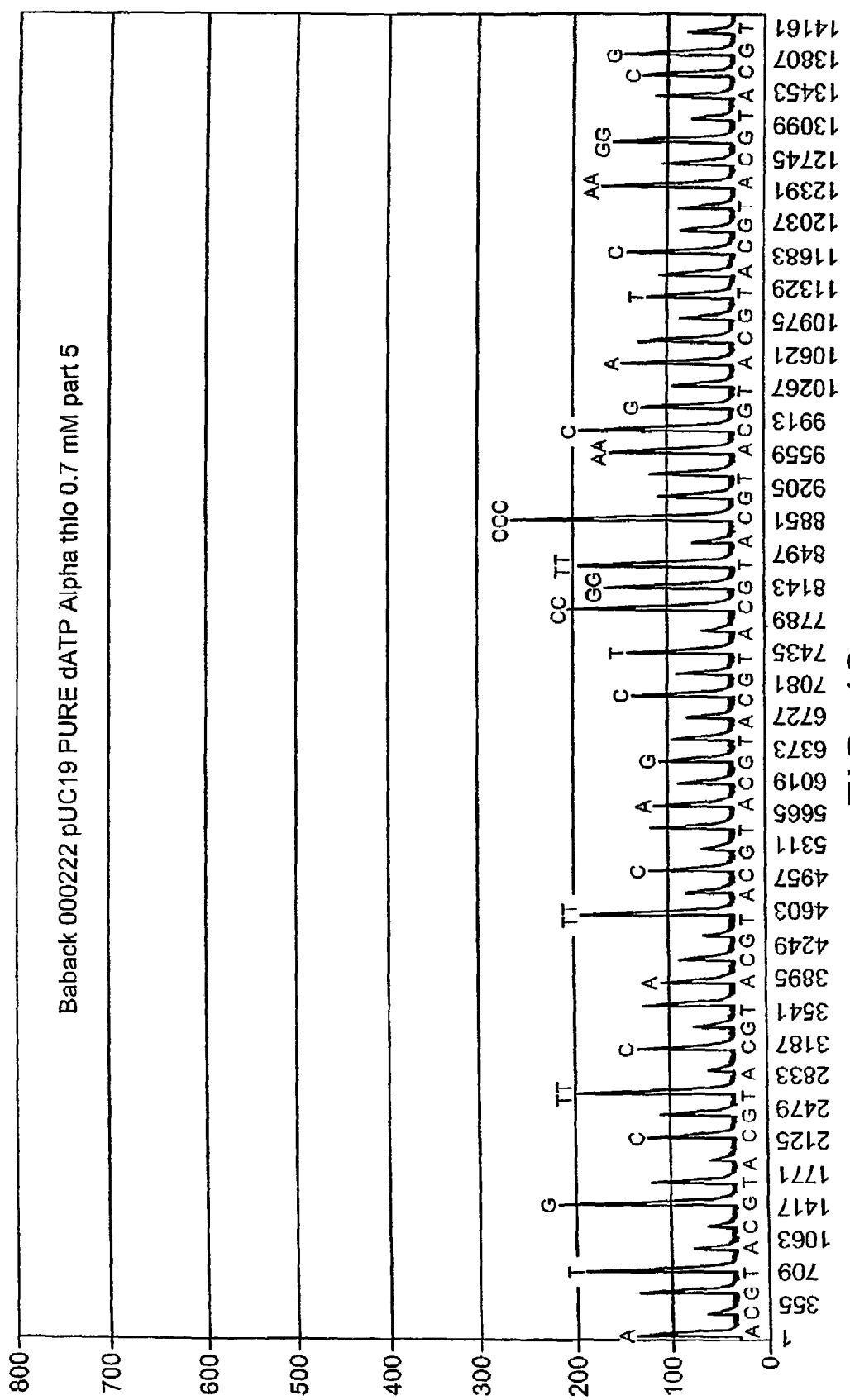
Figure 10:
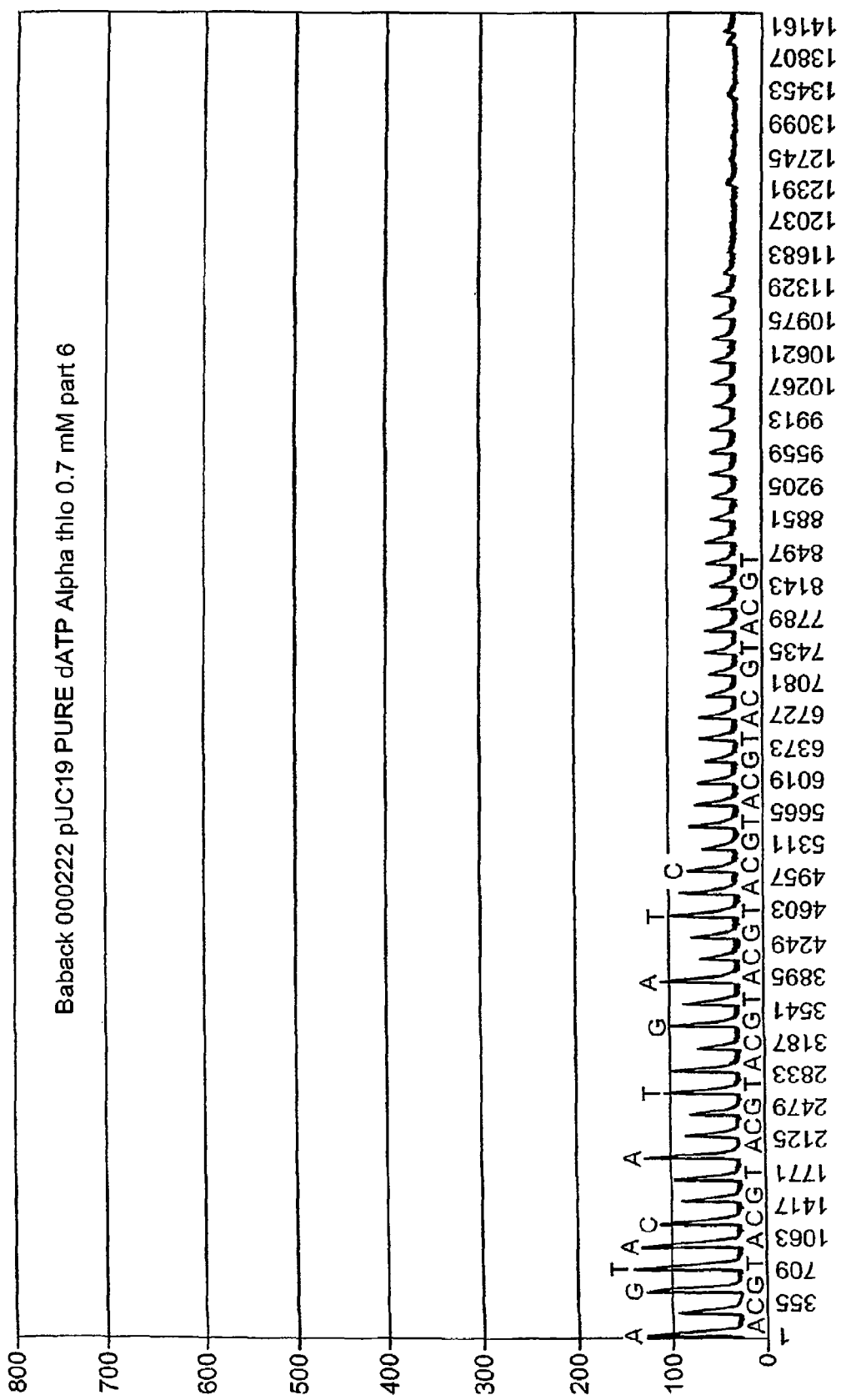

Looking at FIG. 9 it can be seen that signal quality gradually deteriorates with repeated nucleotide addition, leading eventually to loss of readable signal (parts 4-6 of FIG. 9). In FIG. 10, it will be seen that with pure Sp isomer, signal quality is maintained for longer, and a longer read-length is obtained before signal quality deteriorates below readable.

What is claimed is:

1. A kit for use in a method of identifying a base at a target position in a nucleic acid which comprises:
   (a) a polymerase
   (b) means for detecting pyrophosphate release;
   (c) optionally a nucleotide-degrading enzyme;
   (d) alkaline phosphatase;
   (e) the Sp isomer of an α-thiotriphosphate analogue of an adenine nucleotide and optionally one or more Sp isomers of thymine, cytosine or guanine nucleotides; and
   (f) optionally, a test specific primer which hybridizes to sample nucleic acid so that the target position is in close proximity to the 3' end of the primer.

2. A kit for use in a method of identifying a base at a target position in a nucleic acid which comprises:
   (a) a polymerase;
   (b) means for detecting pyrophosphate release;
   (c) optionally a nucleotide-degrading enzyme;
   (d) the Sp isomer of an α-thiotriphosphate analogue of an adenine nucleotide and optionally one or more Sp isomers of thymine, cytosine or guanine nucleotides; and
   (e) optionally, a test specific primer which hybridizes to sample nucleic acid DNA so that the target position is in close proximity to the 3' end of the primer;
   (f) optionally, one or more unmodified thymine, cytosine or guanine nucleotides;
   (g) optionally, alkaline phosphatase.

3. The kit of claim 1, which comprises the Sp isomer of dATPαS or ddATPαS.

4. The kit of claim 1, which comprises a nucleotide-degrading enzyme being apyrase.

5. The kit of claim 2, which comprises a nucleotide-degrading enzyme being apyrase.

6. The kit of claim 1, wherein the polymerase of (a) is DNA polymerase.

7. The kit of claim 2, wherein the polymerase of (a) is DNA polymerase.

8. The kit of claim 1, wherein the means (b) for detecting pyrophosphate release comprises the enzymes luciferase and ATP sulphurylase.

9. The kit of claim 2, wherein the means (b) for detecting pyrophosphate release comprises the enzymes luciferase and ATP sulphurylase.

* * * * *